United States Patent
Leibovich

(10) Patent No.: US 6,187,822 B1
(45) Date of Patent: Feb. 13, 2001

(54) WOUND TREATMENT THROUGH INHIBITION OF ADENOSINE DIPHOSPHATE RIBOSYL TRANSFERASE

(75) Inventor: Samuel J. Leibovich, Livingston, NJ (US)

(73) Assignee: University of Medicine & Dentistry of NJ, Newark, NJ (US)

( * ) Notice: Under 35 U.S.C. 154(b), the term of this patent shall be extended for 0 days.

(21) Appl. No.: 09/332,283

(22) Filed: Jun. 11, 1999

(51) Int. Cl.⁷ .......................... A61K 31/12; A61K 31/35; A61K 31/355

(52) U.S. Cl. .......................... 514/685; 514/681; 514/865; 514/456; 514/458

(58) Field of Search ...................... 514/309, 352, 514/310, 355, 616; 424/84, 401, 532, 426, 456, 94.1, 141.1, 236.1, 184.1; 435/252.3, 69.5; 536/23.1

(56) References Cited

U.S. PATENT DOCUMENTS

| | | | |
|---|---|---|---|
| 3,940,478 | * | 2/1976 | Kurtz ........................... 424/94 |
| 4,725,609 | * | 2/1988 | Kull, Jr. et al. ................ 514/355 |
| 4,933,288 | * | 6/1990 | Greenfield .................... 435/252.3 |
| 4,957,744 | * | 9/1990 | Valle et al. .................... 424/401 |
| 5,213,813 | * | 5/1993 | Kornecki et al. .............. 424/532 |
| 5,215,738 | * | 6/1993 | Lee et al. ..................... 514/352 |
| 5,378,461 | * | 1/1995 | Neigut ......................... 424/94.1 |
| 5,391,376 | * | 2/1995 | Long, Jr. et al. .............. 424/450 |
| 5,468,484 | * | 11/1995 | Hodges et al. ................ 424/141.1 |
| 5,518,730 | * | 5/1996 | Fuisz ........................... 424/426 |
| 5,562,907 | * | 10/1996 | Arnon .......................... 424/236.1 |
| 5,587,384 | * | 12/1996 | Zhang et al. .................. 514/309 |
| 5,602,183 | * | 2/1997 | Martin et al. ................. 514/724 |
| 5,753,702 | * | 5/1998 | Bednar et al. ................. 514/552 |
| 5,756,548 | * | 5/1998 | Flitter et al. .................. 514/616 |
| 5,858,365 | * | 1/1999 | Faller ........................... 424/184.1 |
| 5,866,693 | * | 2/1999 | Laping ......................... 536/23.1 |
| 5,874,444 | * | 2/1999 | West ............................ 514/310 |
| 5,952,197 | * | 9/1999 | Ni et al. ....................... 435/69.5 |
| 5,994,372 | * | 11/1999 | Yaksh .......................... 514/327 |

FOREIGN PATENT DOCUMENTS

638309 * 7/1993 (EP) .
9637227 * 11/1996 (WO) .

OTHER PUBLICATIONS

Shah et al., Complete inhibition of . . . , Biochim. Biophys. Acta, vol. 1312/1, pp. 1–7, 1996.*
Schindl et al., Diabetic neuropathic . . . , Dermatology, vol. 198/3, pp. 314–316, 1999.*
Walgenbach et al., Surgically–induced angiogenesis . . . , Langenbecks archiv . . . , vol. 115, pp. 1186–1188, 1998.*

* cited by examiner

Primary Examiner—William R. A. Jarvis
Assistant Examiner—Vickie Kim
(74) Attorney, Agent, or Firm—Richard R. Muccino

(57) ABSTRACT

The present invention pertains to a method for healing a wound in a mammal which comprises the steps of (A) providing a therapeutic wound healing composition comprising a therapeutically effective amount of an inhibitor of mono-adenosine diphosphate-ribosyl transferase to inhibit adenosine diphosphate-ribosylation of vascular endothelial growth factor; and (B) contacting the therapeutic wound healing composition with a wound in a mammal. This invention also pertains to wound healing compositions and to methods for preparing and using the wound healing compositions and the pharmaceutical products in which the therapeutic compositions may be used. This invention further pertains to therapeutic dermatological-wound healing compositions useful to minimize and treat diaper dermatitis and to methods for preparing and using the therapeutic dermatological-wound healing compositions.

10 Claims, 6 Drawing Sheets

A. RAW Cells

B. MPMs

WOUND TREATMENT THROUGH INHIBITION OF ADENOSINE DIPHOSPHATE RIBOSYL TRANSFERASE

BACKGROUND OF THE INVENTION

1. Field of the Invention

The present invention pertains to a method for healing a wound in a mammal which comprises the steps of (A) providing a therapeutic wound healing composition comprising a therapeutically effective amount of an inhibitor of mono-adenosine diphosphate-ribosyl transferase to inhibit adenosine diphosphate-ribosylation of vascular endothelial growth factor; and (B) contacting the therapeutic wound healing composition with a wound in a mammal. This invention also pertains to wound healing compositions and to methods for preparing and using the wound healing compositions and the pharmaceutical products in which the therapeutic compositions may be used. This invention further pertains to therapeutic dermatological-wound healing compositions useful to minimize and treat diaper dermatitis and to methods for preparing and using the therapeutic dermatological-wound healing compositions.

2. Description of the Background

The disclosures referred to herein to illustrate the background of the invention and to provide additional detail with respect to its practice are incorporated herein by reference and, for convenience, are referenced in the following text and respectively grouped in the appended bibliography.

Wounds are internal or external bodily injuries or lesions caused by physical means, such as mechanical, chemical, viral, bacterial, or thermal means, which disrupt the normal continuity of structures. Such bodily injuries include contusions, wounds in which the skin is unbroken, incisions, wounds in which the skin is broken by a cutting instrument, and lacerations, wounds in which the skin is broken by a dull or blunt instrument. Wounds may be caused by accidents or by surgical procedures. Patients who suffer major or chronic wounds could benefit from an enhancement in the wound healing process. Wound healing consists of a series of processes whereby injured tissue is repaired, specialized tissue is regenerated, and new tissue is reorganized. Wound healing consists of three major phases: a) an inflammation phase (0–3 days), b) a cellular proliferation phase (3–12 days), and (c) a remodeling phase (3 days–6 months). During the inflammation phase, platelet aggregation and clotting form a matrix which traps plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

Macrophages play a key role in the induction of angiogenesis in fibroproliferative states, including wound repair, rheumatoid arthritis, and solid tumor development (1–5). Production of angiogenic activity by macrophages depends on the balance of production of positive angiogenic regulators and inhibitors of angiogenesis (6,7,8). Positive angiogenic regulators previously shown to be produced by monocytes and macrophages include the cytokines TNFα and Il-8 (9,10,11); negative regulators include thrombospondin-1, Ifnγ-inducible protein-10 (γIP-10) and other as yet uncharacterized protein inhibitors (12,13,14). The mechanisms controlling the balance of positive and negative angiogenesis regulators are not well understood. Non-activated monocytes and macrophages exhibit a non-angiogenic phenotype (1,4). Following activation with agents such as interferon-γ and/or endotoxin (LPS), macrophages express angiogenic activity, characterized by the expression of angiogenic cytokines, as well as of inhibitors of angiogenesis (15,16,17,18). Activated cells also produce and release oxygen radicals, nitric oxide (NO) and their derivatives (17,19). These radicals have been shown to play an important role in regulating the angiogenic phenotype of activated macrophages (20,21). Agents such as Ifnγ and LPS, as well as reduced oxygen tension (hypoxia) and elevated lactate levels, induce macrophages to express angiogenic activity (1–3,9,22). Recently, macrophages in vivo have been shown to express vascular endothelial growth factor (VEGF), an endothelial-specific mitogen that is potently angiogenic (18, 23–30).

U.S. Pat. No. 5,510,391 (Elson) discloses a method of treating blood vessel disorders of the skin and skin disorders caused by photo-aging comprising: a) coformulating a pharmaceutical composition wherein the composition contains from 0.01% to 50% vitamin K; and b) applying the pharmaceutical composition topically to treat blood vessel disorders of the skin and skin disorders caused by photo-aging. The blood vessel disorders of the skin and skin disorders caused by photo-aging includes actinic and iatrogenic purpura, lentigines, telangiectasias of the face, spider angiomas, spider veins of the face and leg.

SUMMARY OF THE INVENTION

The present invention pertains to a method for healing a wound in a mammal which comprises the steps of:

(A) providing a therapeutic wound healing composition comprising a therapeutically effective amount of an inhibitor of mono-adenosine diphosphate-ribosyl transferase to inhibit adenosine diphosphate-ribosylation of vascular endothelial growth factor; and (B) contacting the therapeutic wound healing composition with a wound in a mammal.

In a preferred embodiment, the mammal is man. In another preferred embodiment, the inhibitor of mono-adenosine diphosphate-ribosyl transferase is selected from the group consisting of Vitamin K1, Vitamin K2, Vitamin K3, Vitamin K4, Vitamin K5, Vitamin K6, Novobiocin, m-iodo benzyl guanidine, nicotinamide, coumermycin, dicoumarol, and silybin. More preferred inhibitors of mono-adenosine diphosphate-ribosyl transferase are Vitamin K1, Vitamin K3, Novobiocin, and silybin. The inhibitor of mono-adenosine diphosphate-ribosyl transferase is present in the therapeutic wound healing composition in an amount from about 0.1% to about 10%, by weight of the therapeutic wound healing composition. The wound may be selected from the group consisting of pressure ulcers, decubitus ulcers, diabetic ulcers, and burn injuries. The therapeutic wound healing composition may further comprise a pharmaceutically acceptable carrier.

The present invention also pertains to a wound healing composition which comprises:

(A) a therapeutically effective amount of an inhibitor of mono-adenosine diphosphate-ribosyl transferase to inhibit adenosine diphosphate-ribosylation of vascular endothelial growth factor; and (B) a pharmaceutically acceptable carrier.

The present invention further pertains to a method for treating diaper dermatitis in a human which comprises the steps of:

(A) providing a therapeutic diaper dermatitis wound healing composition comprising:

(a) a therapeutically effective amount of an inhibitor of mono-adenosine diphosphate-ribosyl transferase to inhibit adenosine diphosphate-ribosylation of vascular endothelial growth factor;

(b) a buffering agent to maintain the pH of dermatitis in a range from about 5 to about 8; and (c) an anti-inflammatory agent; and (B) contacting the therapeutic diaper dermatitis wound healing composition with diaper dermatitis in a human.

The present invention further pertains to a therapeutic dermatological-wound healing composition useful to minimize and treat diaper dermatitis which comprises a therapeutically effective amount of:

(1) a therapeutic wound healing composition comprising an inhibitor of mono-adenosine diphosphate-ribosyl transferase to inhibit adenosine diphosphate-ribosylation of vascular endothelial growth factor;

(2) a buffering agent to maintain the pH of dermatitis in a range from about 5 to about 8; and (3) an anti-inflammatory agent.

DETAILED DESCRIPTION OF THE INVENTION

Figure 1:
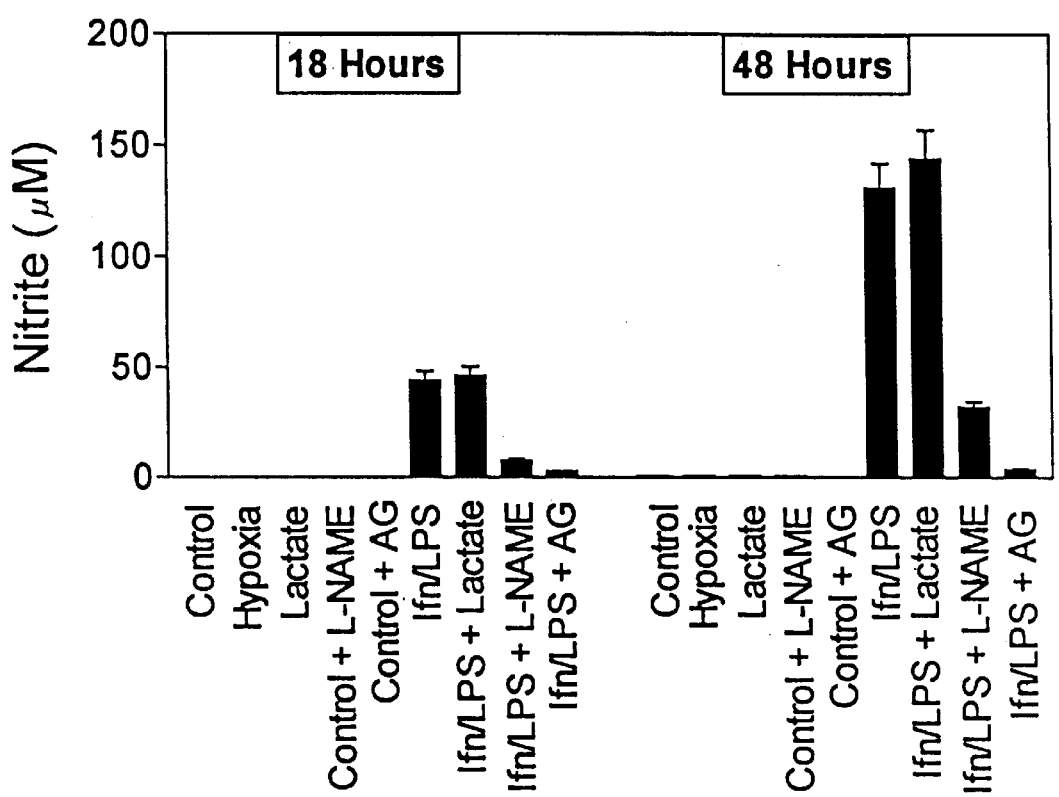
FIG. 1 illustrates the nitrite production by MPMs.

Production of macrophage-dependent angiogenic activity (MDAA) requires activation by factors such as Interferon-γ and/or endotoxin, hypoxia or high concentrations of lactate (Jensen et al. Lab. Invest. 54, 574, 1986). Previous work has demonstrated that the inducible nitric oxide synthase (iNOS) pathway in macrophages regulates MDAA, with inhibition of iNOS down-regulating expression of MDAA (Leibovich et al, PNAS USA 91, 4190, 1994). It has now been found that although non-activated macrophages are non-angiogenic, they nevertheless express significant levels of the angiogenic growth factor VEGF. This constitutive expression of VEGF is not hypoxia or lactate dependent. The VEGF produced constitutively by normoxic, non-activated macrophages is found to be in a non-angiogenic form, due to post-translational modification by the process of arginine-specific ADP-ribosylation. In contrast, VEGF produced by LPS-activated, hypoxic, or lactate-treated macrophages is in the non-ADP-ribosylated form, and is angiogenic. Inhibition of the iNOS pathway in LPS-activated macrophages abrogates MDAA expression by a dual mechanism. First, VEGF reverts to the ADP-ribosylated, non-angiogenic state; second, iNOS-inhibited macrophages express an anti-angiogenic factor that blocks the angiogenic activity of several angiogenic factors, including VEGF, TNFα and bFGF. In mice where the iNOS gene has been specifically deleted (iNOS knockout mice, iNOS−/−), wound repair is markedly inhibited (Yamasaki et al., J. Clin. Invest. 101, 967, 1998). This inhibition is manifested in delayed wound closure, and a delay in the formation of granulation tissue. Macrophages from iNOS−/− mice express reduced levels of MDAA in comparison to iNOS+/+ mice, although total VEGF production is not markedly altered. The role of the iNOS pathway and ADP-ribosylation of VEGF in regulating angiogenesis in wound repair and the modalities for pharmacologically modulating macrophage-dependent angiogenic activity and wound repair by targeting iNOS and ADP-ribosylation pathways are under investigation.

Murine thioglycolate-induced peritoneal macrophages (MPMs) and the murine RAW264.7 macrophage-like cell line (RAW cells) constitutively produce vascular endothelial growth factor (VEGF). VEGF production is increased under hypoxic conditions or following cell activation with interferon-γ (Ifnγ) and endotoxin (LPS). In contrast, TNFα, is produced only by Ifnγ/LPS-activated cells. Lactate (20 mM) does not increase VEGF production by these cells. However, hypoxia, lactate, and Ifnγ/LPS-activated MPMs express angiogenic activity, while normoxic, non-activated MPMs do not. Lack of angiogenic activity is not due to an anti-angiogenic factor(s) in the medium of these cells. Angiogenic activity produced by hypoxia and lactate-treated MPMs is neutralized by anti-VEGF antibody, which also neutralizes most of the angiogenic activity produced by Ifnγ/LPS-activated MPMs. The inducible nitric oxide synthase (iNOS) inhibitors $N^g$ nitro-L-arginine-methyl ester (L-NAME) (1.5 mM) and aminoguanidine (AG)(1 mM) block production of angiogenic activity by MPMs and RAW cells. In RAW cells, L-NAME and AG block Ifnγ/LPS-activated, but not constitutive VEGF production, while in MPMs, neither constitutive nor Ifnγ/LPS-activated VEGF synthesis is affected. Synthesis of TNFα is also unaffected. In contrast to normoxic, non-activated MPMs, iNOS-inhibited, Ifnγ/LPS-activated MPMs produce an anti-angiogenic factor(s). Accordingly, VEGF is a major contributor to macrophage-derived angiogenic activity, and that activation by hypoxia, lactate or Ifnγ/LPS switches macrophage-derived VEGF from a non-angiogenic to an angiogenic state. This switch may involve a post-translational modification of VEGF, possibly by the process of ADP-ribosylation. ADP-ribosylation by MPM cytosolic extracts or by cholera toxin switches $rVEGF_{165}$ from an angiogenic to a non-angiogenic state. In Ifnγ/LPS-activated MPMs, the iNOS-dependent pathway also regulates the expression of an anti-angiogenic factor(s) that antagonizes the bio-activity of VEGF and provides an additional regulatory pathway controlling the angiogenic phenotype of macrophages.

In accord with the present invention, the expression of the angiogenic growth factor VEGF by MPMs and RAW cells was examined, and compared with that of TNFα. The effects of hypoxia, lactate and the L-arginine-dependent inducible NO-synthase (iNOS) pathway on the production of VEGF and TNFα by these cells was also examined. VEGF production was found to be regulated both transcriptionally and translationally by hypoxia and the iNOS pathway, and post-translational modification may play an important role in regulating the bio-activity of VEGF as an angiogenic factor. In addition, the iNOS pathway in Ifnγ/LPS-activated macrophages regulates the expression of anti-angiogenic factor that antagonizes the angiogenic effects of VEGF, providing an additional regulatory pathway to control the angiogenic phenotype of macrophages.

Vascular endothelial growth factor (VEGF), a polypeptide growth factor that is potently angiogenic (induces the growth of new blood vessels), is chemically modified by macrophages (a cell that plays a key role in regulating angiogenesis) in wound repair. This chemical modification involves the ADP-ribosylation of VEGF by enzymes (ADP-ribosyl transferases) in macrophages. In particular, the cytoplasmic mono-ADP-ribosyl transferases are involved in ADP-ribosylation of VEGF, and this modification results in a change in the properties of the VEGF from being angiogenic to being non-angiogenic. Macrophages make VEGF constitutively, and it seems that macrophages regulate the angiogenic activity of VEGF by this ADP-ribosylation reaction. Inhibitors of mono-ADP-ribosylation such as: Vitamin K1, Vitamin K2, Vitamin K3, Novobiocin, m-iodo benzyl guanidine, and nicotinamide change the phenotype of macrophages from a non-angiogenic to an angiogenic phenotype by inhibiting the ADP-ribosylation of VEGF. Since angiogenesis induction is a key event in normal wound repair, VEGF production by macrophages, the key cells that control angiogenesis by producing angiogenic factors, must require a switch from the non-angiogenic to the angiogenic phenotype, that is, from the ADP-ribosylated to the non-modified form.

Since the inhibitors of mono-ADP-ribosylation can block the ADP-ribosylation of VEGF, these inhibitors, and their derivatives and analogs are valuable in the treatment of chronic, non-healing wounds, where angiogenesis is deficient. In many chronic wounds, including but not limited to, pressure ulcers, decubitus ulcers, diabetic ulcers, and certain burn injuries, wounds fail to heal, at least in part due to failures in angiogenesis. The macrophage phenotype in these wounds may be non-angiogenic, with VEGF being produced in the non-angiogenic, ADP-ribosylated form. In this case, treatment of these wounds with inhibitors of ADP-ribosylation would block the ADP-ribosylation of VEGF, and thus result in the production of non-modified, angiogenic VEGF. This VEGF should then participate in stimulating angiogenesis in the wounds, and help promote repair. Accordingly, the present invention is directed to a formulation of ADP-ribosyl transferase inhibitors in an appropriate vehicle suitable for local application to wounds.

Present technology for the treatment of chronic wounds generally involves intensive wound care, debridement, use of antiseptics, antibiotics, and the use of occlusive dressings. Technologies in development include the use of growth factors, usually prepared by genetic engineering using recombinant DNA technology. Growth factor therapy is currently in clinical trials. Growth factors are extremely expensive, and their efficacy is still in doubt. The advantages of the use of ADP-ribosylation inhibitors for the treatment of chronic wounds are: a) the compounds are low molecular weight, well characterized, available, and relatively cheap; b) the compounds modulate the bio-activity of the wound's own biological mediators, shifting them from being non-angiogenic to being angiogenic, rather than attempting to introduce an exogenous growth factor activity; c) formulation of low molecular weight inhibitors for delivery to wounds should be a relatively simple exercise, certainly compared to the formulation of growth factors; and d) vitamin-K compounds, which constitute one of the major groups of mono-ADP ribosylation inhibitors, have been available for other purposes for many years, and have FDA approval.

As set out above, the present invention is directed to a method for healing a wound in a mammal which comprises the steps of (A) providing a therapeutic wound healing composition comprising a therapeutically effective amount of an inhibitor of mono-adenosine diphosphate-ribosyl transferase to inhibit adenosine diphosphate-ribosylation of vascular endothelial growth factor; and (B) contacting the therapeutic wound healing composition with a wound in a mammal.

The inhibitor of mono-adenosine diphosphate-ribosyl transferase may be any inhibitor, including active derivatives and analogs, which inhibits ADP-ribosylation of vascular endothelial growth factor, thereby switching vascular endothelial growth factor from the non-angiogenic form to the angiogenic phenotype, that is, from the ADP-ribosylated form to the non-ADP-ribosylated form. Preferably, the inhibitor of mono-adenosine diphosphate-ribosyl transferase is selected from the group consisting of Vitamin K1, Vitamin K2, Vitamin K3, Vitamin K4, Vitamin K5, Vitamin K6, Novobiocin, m-iodo benzyl guanidine, nicotinamide, coumermycin, dicoumarol, and silybin. More preferably, the inhibitor of mono-adenosine diphosphate-ribosyl transferase is selected from the group consisting of Vitamin K1, Vitamin K3, Novobiocin, and silybin.

The amount of inhibitor of mono-adenosine diphosphate-ribosyl transferase present in the therapeutic wound healing compositions of the present invention is a therapeutically effective amount. A therapeutically effective amount of inhibitor of mono-adenosine diphosphate-ribosyl transferase is that amount of inhibitor of mono-adenosine diphosphate-ribosyl transferase necessary for the inventive composition to switch the vascular endothelial growth factor from the non-angiogenic form to the angiogenic phenotype, that is, from the ADP-ribosylated form to the non-ADP-ribosylated form, and thereby promote wound healing. The exact amount of inhibitor of mono-adenosine diphosphate-ribosyl transferase is a matter of preference subject to such factors as the type of condition being treated as well as the other ingredients in the composition. In a preferred embodiment, inhibitor of mono-adenosine diphosphate-ribosyl transferase is present in the therapeutic wound healing composition in an amount from about 0.1% to about 10%, preferably from about 0.2% to about 8%, and more preferably from about 0.3% to about 5%, by weight of the therapeutic wound healing composition.

The types of wounds which may be healed using the wound healing compositions of the present invention are those which result from an injury which causes epidermal damage such as incisions, wounds in which the skin is broken by a cutting instrument, and lacerations, wounds in which the skin is broken by a dull or blunt instrument. The therapeutic compositions may be used to treat pressure ulcers, decubitus ulcers, diabetic ulcers, and burn injuries. The therapeutic compositions may also be used to treat various dermatological disorders such as hyperkeratosis, burns, donor site wounds from skin transplants, ulcers (cutaneous, decubitis, venous stasis, and diabetic), psoriasis, skin rashes, and sunburn photoreactive processes. The wound healing compositions can be used for the following indications: a) Healing of cuts and scrapes; b) Burns (heals burns with less scaring and scabbing); c) Decubitus ulcers; d) Bed sores, pressure ulcers; e) Fissures, Hemorrhoids; f) Use in combination with immunostimulators (simulated healing in healing deficient people); g) Post surgical wounds; h) Bandages; i) Diabetic ulcers; j) Venous ulceration; and k) Use in combination with wound cleansing agents. Preferably, the therapeutic compositions may be used to treat pressure ulcers, decubitus ulcers, diabetic ulcers, and burn injuries.

In another embodiment, the present invention is directed to a wound healing composition which comprises (A) a therapeutically effective amount of an inhibitor of mono-adenosine diphosphate-ribosyl transferase to inhibit adenosine diphosphate-ribosylation of vascular endothelial growth factor; and (B) a pharmaceutically acceptable carrier, wherein the amount and type of inhibitor of mono-adenosine diphosphate-ribosyl transferase to inhibit adenosine diphosphate-ribosylation of vascular endothelial growth factor are set out above.

In a specific embodiment, the present invention is directed to diaper dermatitis. Diaper dermatitis, or diaper rash, is an irritant contact dermatitis localized to the skin area in contact with the diaper in infants. Diaper dermatitis occurs in about 65% of infants ranging from one to 20 months of age. The manifestations of diaper dermatitis vary from diff-use erythema to nodular lesions. Prolonged contact of the skin with urine-soaked diapers results in maceration of the epidermis. Occlusive rubber or plastic pants further aggravates the injury. Diaper dermatitis is caused by ammonia from the urine raising the pH of the skin and combining with constituents of skin oil to form irritants. Bacterial or yeast infections may further complicate diaper dermatitis by causing persistent and severe inflammation. Diaper dermatitis is generally treated by keeping the skin dry by changing diapers frequently and applying talcum powder to the irritated area. In severe cases, rubber pants and plastic disposable diaper coverings should be avoided.

In accord with the present invention, a method for treating diaper dermatitis in a human is provided which comprises the steps of (A) providing a therapeutic diaper dermatitis wound healing composition comprising: (a) a therapeutically effective amount of an inhibitor of mono-adenosine diphosphate-ribosyl transferase to inhibit adenosine diphosphate-ribosylation of vascular endothelial growth factor; (b) a buffering agent to maintain the pH of dermatitis in a range from about 5 to about 8; and (c) an anti-inflammatory agent; and (B) contacting the therapeutic diaper dermatitis wound healing composition with diaper dermatitis in a human. Buffering agents can help prevent diaper dermatitis by neutralizing ammonia but do not heal injured mammalian cells. Anti-inflammatory agents can reduce inflammation (erythema) in a patient but do not promote the wound healing process. Wound healing compositions can increase the resuscitation rate of injured mammalian cells and the proliferation rate of new mammalian cells to replace dead cells. Applicants have found that the combination of a buffering agent, an anti-inflammatory agent, and a wound healing composition results in a therapeutic dermatological-wound healing compositions useful for minimizing and treating diaper dermatitis. The dermatological-wound healing compositions may optionally contain a therapeutically effective amount of a topical antiseptic to further reduce the duration and severity of diaper dermatitis.

Buffering agents are solute compounds which will form a solution to which moderate amounts of either a strong acid or base may be added without causing a large change in the pH value of the solution. In Bronsted's terminology, a buffering agent contains both a weak acid and its conjugate weak base. Buffering solutions usually contain (a) a weak acid and a salt of the weak acid, (b) a mixture of an acid salt with the normal salt, or (c) a mixture of two acid salts, for example $NaH_2PO_4$ and $Na_2HPO_4$. A weak acid becomes a buffering agent when alkali is added and a weak base becomes a buffering agent when acid is added. The buffering agents in the dermatological-wound healing compositions of the present invention may be selected from a wide range of therapeutic agents and mixtures of therapeutic agents. Buffering agents which occur in nature include phosphates, carbonates, ammonium salts, proteins of plant and animal tissues, and the carbonic-acid-bicarbonate system in blood. Nonlimiting illustrative specific examples of buffering agents include citric acid-sodium citrate solution, phosphoric acid-sodium phosphate solution, and acetic acid-sodium acetate solution. Preferably, the buffering agent is phosphoric acid-sodium phosphate.

The amount of buffering agent used in the present invention is an effective amount and may vary depending upon the dosage recommended or permitted for the particular buffering agent. In general, the amount of buffering agent present is the ordinary dosage required to obtain the desired result. Such dosages are known to the skilled practitioner in the medical arts and are not a part of the present invention. In a preferred embodiment, the buffering agent in the dermatological-wound healing composition is present in an amount to maintain the pH of the dermatitis in a range from about 5 to about 8, preferably from about 5.5 to about 7.5, and more preferably from about 6 to about 7.

Anti-inflammatory agents are compounds that counteract or suppress the inflammatory process. The anti-inflammatory agents in the dermatological-wound healing compositions of the present invention may be selected from a wide variety of steroidal, non-steroidal, and salicylate water-soluble and water-insoluble drugs and their acid addition or metallic salts. Both organic and inorganic salts may be used provided the anti-inflammatory agent maintains its medicament value. The anti-inflammatory agents may be selected from a wide range of therapeutic agents and mixtures of therapeutic agents which may be administered in sustained release or prolonged action form. Nonlimiting illustrative specific examples of non-steroidal anti-inflammatory agents include the following medicaments: ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, and evening primrose oil (containing about 72% linoleic acid and about 9% gamma-linolenic acid). Nonlimiting illustrative specific examples of salicylate anti-inflammatory agents include the following medicaments: acetylsalicylic acid, mesalamine, salsalate, diflunisal, salicylsalicylic acid, and choline magnesium trisalicylate. Nonlimiting illustrative specific examples of steroidal anti-inflammatory agents include the following medicaments: flunisolide, triamcinoline, triamcinoline acetonide, beclomethasone diproprionate, betamethasone diproprionate, hydrocortisone, cortisone, dexamethasone, predinisone, methyl prednisolone, and prednisolone.

Preferred anti-inflammatory agents to be employed may be selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone diproprionate, betamethasone diproprionate, hydrocortisone, cortisone, dexamethasone, predinisone, methyl prednisolone, and prednisolone. In a preferred embodiment, the anti-inflammatory agent is selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, and evening primrose oil. In a more preferred embodiment, the anti-inflammatory agent is evening primrose oil.

The anti-inflammatory agent of the present invention may be used in many distinct physical forms well known in the pharmaceutical art to provide an initial dosage of the anti-inflammatory agent and/or a further time-release form of the anti-inflammatory agent. Without being limited thereto, such physical forms include free forms and encapsulated forms, and mixtures thereof.

The amount of anti-inflammatory agent used in the present invention is a therapeutically effective amount and may vary depending upon the therapeutic dosage recommended or permitted for the particular anti-inflammatory agent. In general, the amount of anti-inflammatory agent present is the ordinary dosage required to obtain the desired result. Such dosages are known to the skilled practitioner in the medical arts and are not a part of the present invention. In a preferred embodiment, the anti-inflammatory agent in the dermatological-wound healing composition is present in an amount from about 0.01% to about 10%, preferably from about 0.1% to about 5%, and more preferably from about 1% to about 3%, by weight.

In another specific embodiment, the present invention is directed to a therapeutic dermatological-wound healing composition useful to minimize and treat diaper dermatitis which comprises a therapeutically effective amount of:

(1) a therapeutic wound healing composition comprising an inhibitor of mono-adenosine diphosphate-ribosyl transferase to inhibit adenosine diphosphate-ribosylation of vascular endothelial growth factor;

(2) a buffering agent to maintain the pH of dermatitis in a range from about 5 to about 8; and (3) an anti-inflammatory agent.

Once prepared, the inventive therapeutic wound healing compositions may be stored for future use or may be formulated in effective amounts with pharmaceutically acceptable carriers to prepare a wide variety of pharmaceutical compositions. Examples of pharmaceutically acceptable carriers are pharmaceutical appliances and topical vehicles. Examples of pharmaceutical appliances are sutures, staples, gauze, bandages, burn dressings, artificial skins, liposome or micell formulations, microcapsules, aqueous vehicles for soaking gauze dressings, and the like, and mixtures thereof Topical compositions employ topical vehicles, such as creams, gels formulations, foams, ointments and sprays, salves, and films, which are intended to be applied to the skin or body cavity and are not intended to be taken by mouth. Oral topical compositions employ oral vehicles, such as mouthwashes, rinses, oral sprays, suspensions, and dental gels, which are intended to be taken by mouth but are not intended to be ingested. The preferred topical vehicles are water and pharmaceutically acceptable water-miscible organic solvents such as ethyl alcohol, isopropyl alcohol, propylene glycol, glycerin, and the like, and mixtures of these solvents. Water-alcohol mixtures are particularly preferred and are generally employed in a weight ratio from about 1:1 to about 20:1, preferably from about 3:1 to about 20:1, and most preferably from about 3:1 to about 10:1, respectively.

A variety of traditional ingredients may optionally be included in the pharmaceutical composition in effective amounts such as buffers, preservatives, tonicity adjusting agents, antioxidants, polymers for adjusting viscosity or for use as extenders, and excipients, and the like. Other conventional additives include humectants, emollients, lubricants, stabilizers, dyes, and perfumes, providing the additives do not interfere with the therapeutic properties of the therapeutic wound healing composition. Specific illustrative examples of such traditional ingredients include acetate and borate buffers; thimerosol, sorbic acid, methyl and propyl paraben and chlorobutanol preservatives; sodium chloride and sugars to adjust the tonicity; and excipients such as mannitol, lactose and sucrose. Other conventional pharmaceutical additives known to those having ordinary skill in the pharmaceutical arts may also be used in the pharmaceutical composition. The ultimate pharmaceutical compositions are readily prepared using methods generally known in the pharmaceutical arts.

In accordance with this invention, therapeutically effective amounts of the therapeutic wound healing compositions of the present invention may be employed in the pharmaceutical appliance. These amounts are readily determined by those skilled in the art without the need for undue experimentation. The exact amount of the therapeutic wound healing composition employed is subject to such factors as the type and concentration of the therapeutic wound healing composition and the type of pharmaceutical appliance employed. Thus, the amount of therapeutic wound healing composition may be varied in order to obtain the result desired in the final product and such variations are within the capabilities of those skilled in the art without the need for undue experimentation. In a preferred embodiment, the pharmaceutical composition will comprise the therapeutic wound healing composition in an amount from about 0.1% to about 10%, by weight of the pharmaceutical composition. In a more preferred embodiment, the pharmaceutical composition will comprise the therapeutic wound healing composition in an amount from about 0.2% to about 8%, by weight of the pharmaceutical composition. In a most preferred embodiment, the pharmaceutical composition will comprise the therapeutic wound healing composition in an amount from about 0.3% to about 5%, by weight of the pharmaceutical composition.

The present invention extends to methods for making the pharmaceutical compositions. In general, a pharmaceutical composition is made by contacting a therapeutically effective amount of a therapeutic wound healing composition with a pharmaceutically acceptable carrier and the other ingredients of the final desired pharmaceutical composition. The therapeutic wound healing composition may be in a solvent and may be absorbed onto a pharmaceutical appliance.

RESULTS

Production of Nitrite by RAW264.7 Cells and MPMs

FIG. 1 shows the production of nitrite by MPMs. Nitrite was not produced by non-activated cells, either with or without lactate. Following challenge with Ifnγ/LPS, nitrite production was strongly induced, with nitrite accumulating over the 48 hr. incubation period. L-NAME (1.5 mM) blocked nitrite production by about 70–80%; AG (1 mM) blocked nitrite production by >95%. RAW264.7 cells produced nitrite in a similar manner, and L-NAME and AG blocked nitrite synthesis by RAW264.7 cells to a similar extent (data not shown).

Production of VEGF by RAW264.7 Cells and Murine Peritoneal Macrophages

The production of VEGF by RAW cells is shown in FIG. 2A. Non-stimulated RAW cells produced VEGF in an apparently constitutive manner over the 48 hour incubation period. This spontaneous production of VEGF was similar in regular culture plates and in gas-permeable Permanox plates. Stimulation of cells with Ifnγ and LPS increased the production of VEGF by RAW cells over the constitutive level produced by non-stimulated cells by about 3–4 fold by 18 hours. By 48 hours, the stimulated VEGF levels were only 2 fold increased over the constitutive level. The iNOS inhibitors AG (1.0 mM) and L-NAME (1.5 mM) did not block the constitutive production of VEGF by non-stimulated RAW cells, but reduced the production of VEGF by Ifnγ/LPS-activated RAW cells, to a level markedly below that of the non-stimulated cells. Sodium lactate (25 mM) did not alter the production of VEGF by these cells, either with or without Ifnγ/LPS activation. RAW cells cultured under hypoxic conditions produced increased amounts of VEGF. After 18 hours, VEGF levels in the media of cells cultured under hypoxic conditions were about 3 fold greater than those in the media of control, normoxic cells. This differential was less marked by 48 hours. Analyses of the dissolved oxygen levels in the conditioned media directly following harvesting indicated clearly that under normoxic conditions, oxygen levels were consistently high ($pO_2$>145). After 24 and 48 hours incubation under hypoxic conditions (95% $N_2$/5% $CO_2$), the $pO_2$ was 71 mm and 46 mm respectively.

The production of VEGF by MPMs was similar to that of RAW cells, with constitutive production occurring over 48 hours (FIG. 2B). Increased production was induced by Ifnγ/LPS. However, in contrast to RAW cells, iNOS inhibitors did not significantly reduce the production of VEGF by Ifnγ/LPS-activated MPMs. As was observed for RAW cells, sodium lactate did not modulate the production of VEGF by these cells. Culture of MPMs under hypoxic conditions resulted in an increase in VEGF production in the first 18 hours; after 48 hours, however, constitutive production of VEGF was only slightly higher than that of hypoxic cells. Oxygen levels determined in the conditioned media of MPMs were similar to those found in RAW cell media.

Quantitative RT-PCR Analysis of VEGF mRNA Levels

Figure 3:
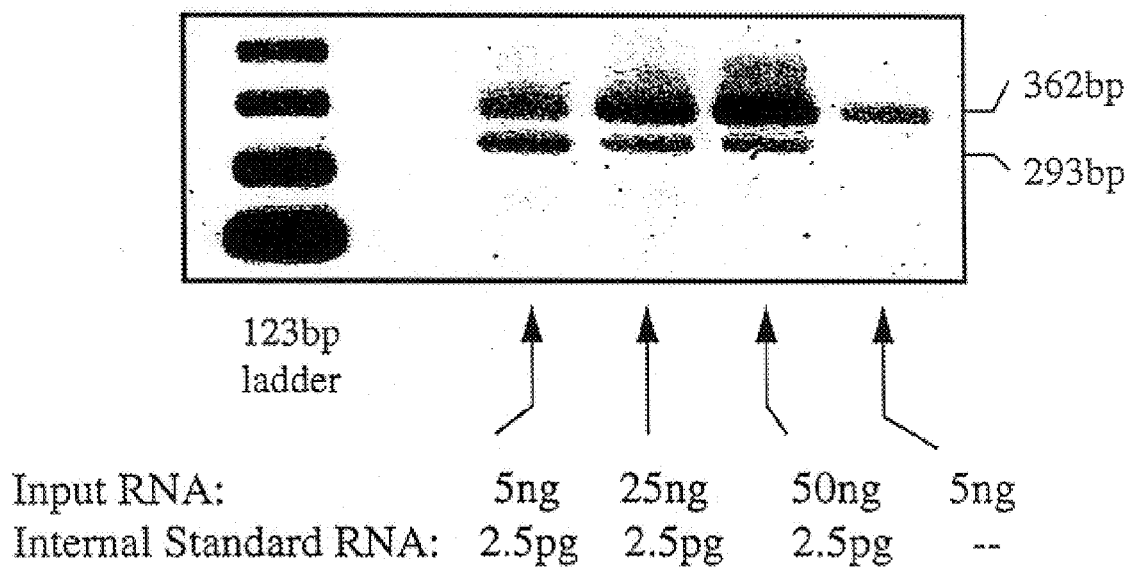
FIG. 3 illustrates competitive RT-PCR analysis of VEGF mRNA levels in control (non-stimulated) MPMs 24 hours following plating.

A typical example of a quantitative RT-PCR dilution series using the VEGF RNA minigene as internal standard is shown in FIG. 3. The PCR amplification product of the minigene is 293 bp in size. The native mRNA PCR amplification band is 362 bp in size. The point of equivalence for the amplified minigene and the amplified native mRNA is readily determined from the dilution series. The values determined from these analyses were normalized to the levels of G3PDH mRNA determined in parallel samples, although little variation in the G3PDH mRNA levels were in fact observed between samples. On this basis, the relative amounts of VEGF mRNA in the various macrophage preparations are shown in Table 1. Both hypoxia and Ifnγ/LPS activation upregulated VEGF steady state mRNA levels in MPMs at 4 and 10 hours. By 24 hours, however, the levels of VEGF mRNA were similar in all the groups. In RAW cells, VEGF mRNA levels remained elevated at 24 hours. Aminoguanidine treatment of Ifnγ/LPS-treated MPMs did not significantly reduce their steady-state VEGF mRNA levels at any time point; in RAW cells, however, the VEGF mRNA levels were reduced by 70–80% at 4, 10 and 24 hours.

RT-PCR Analysis of VEGF mRNA Isoforms

Figure 4:
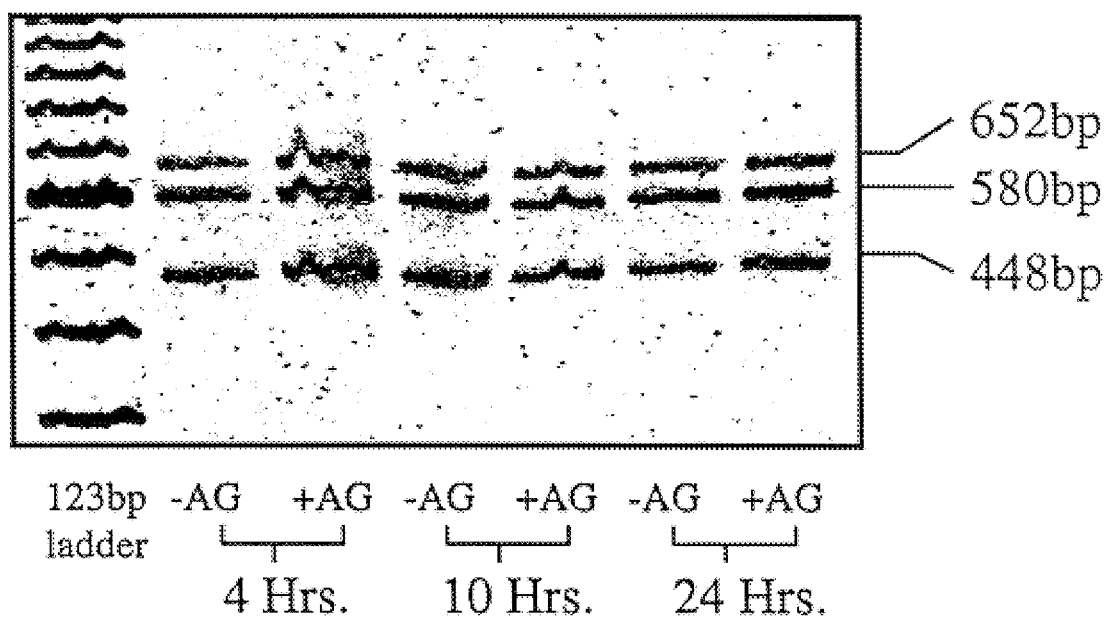
FIG. 4 illustrate RT-PCR analysis of VEGF isoforms produced by Ifnγ/LPS-activated MPMs, with or without AG treatment.

Three isoforms of VEGF were found to be produced by both non-activated and Ifnγ/LPS-activated MPMs. These isoforms corresponded to VEGF-1 (652 bp), VEGF-2 (580 bp) and VEGF-3 (448 bp)(45). The relative proportions of the VEGF isoforms expressed by MPMs at each time point following Ifnγ/LPS activation were only slightly modulated by Ifnγ/LPS-activation and by inhibition of iNOS with AG (FIG. 4). In RAW cells, VEGF mRNA isoforms were similarly unaffected by Ifnγ/LPS activation and by AG treatment.

Production of TNFα by MPMs and RAW264.7 Cells

Figure 5:
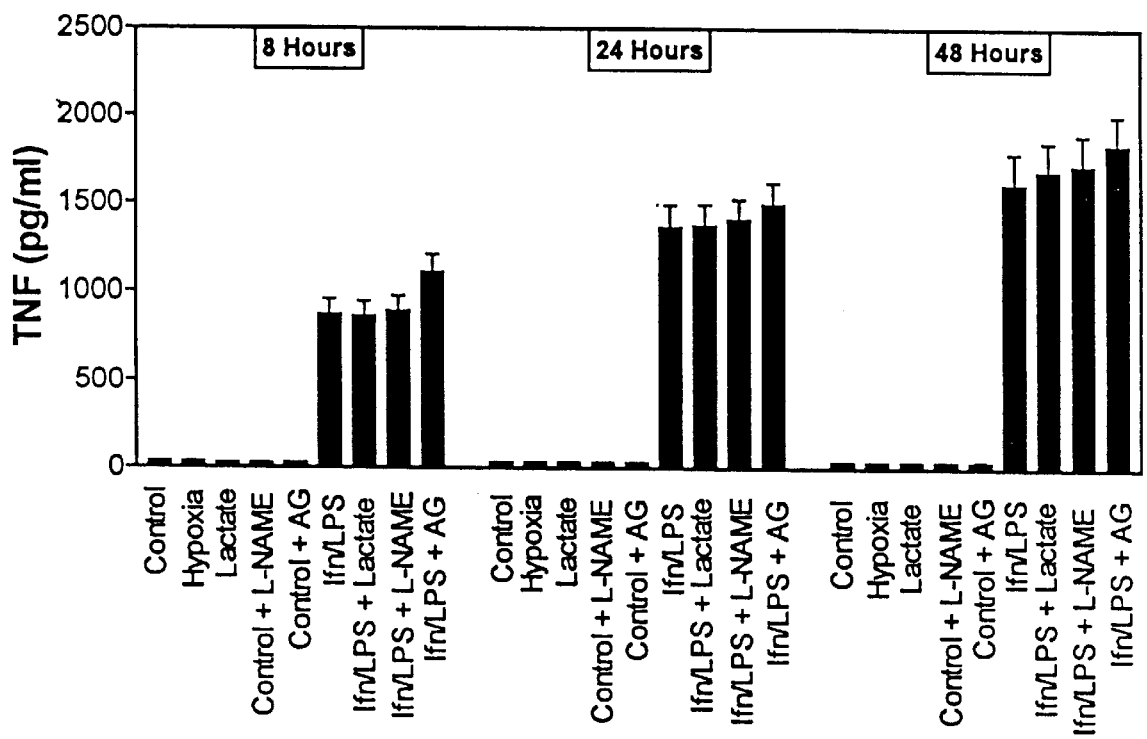
FIG. 5 illustrates TNFα production by MPMs.

TNFα was not produced by either non-stimulated MPMs or by RAW264.7 cells over the 48 hour test period. Production of TNFα by MPMs is shown in FIG. 5. Following stimulation with Ifnγ/LPS, TNFα expression was strongly induced, with increased TNFα in the conditioned media being apparent by 8 hours following challenge. There was no significant difference in TNFα production in cells treated with or without sodium lactate. Similarly, culture of cells in Permanox dishes, under either normoxic or hypoxic conditions, did not modulate TNFα production. The iNOS inhibitors L-NAME and AG had no significant effect on the production of TNFα by MPMs. Production of TNFα by RAW cells was similar to that observed in MPMs (data not shown).

ADP-Ribosylation of VEGF by Bacterial Toxins and Macrophage Extracts

Figure 6:
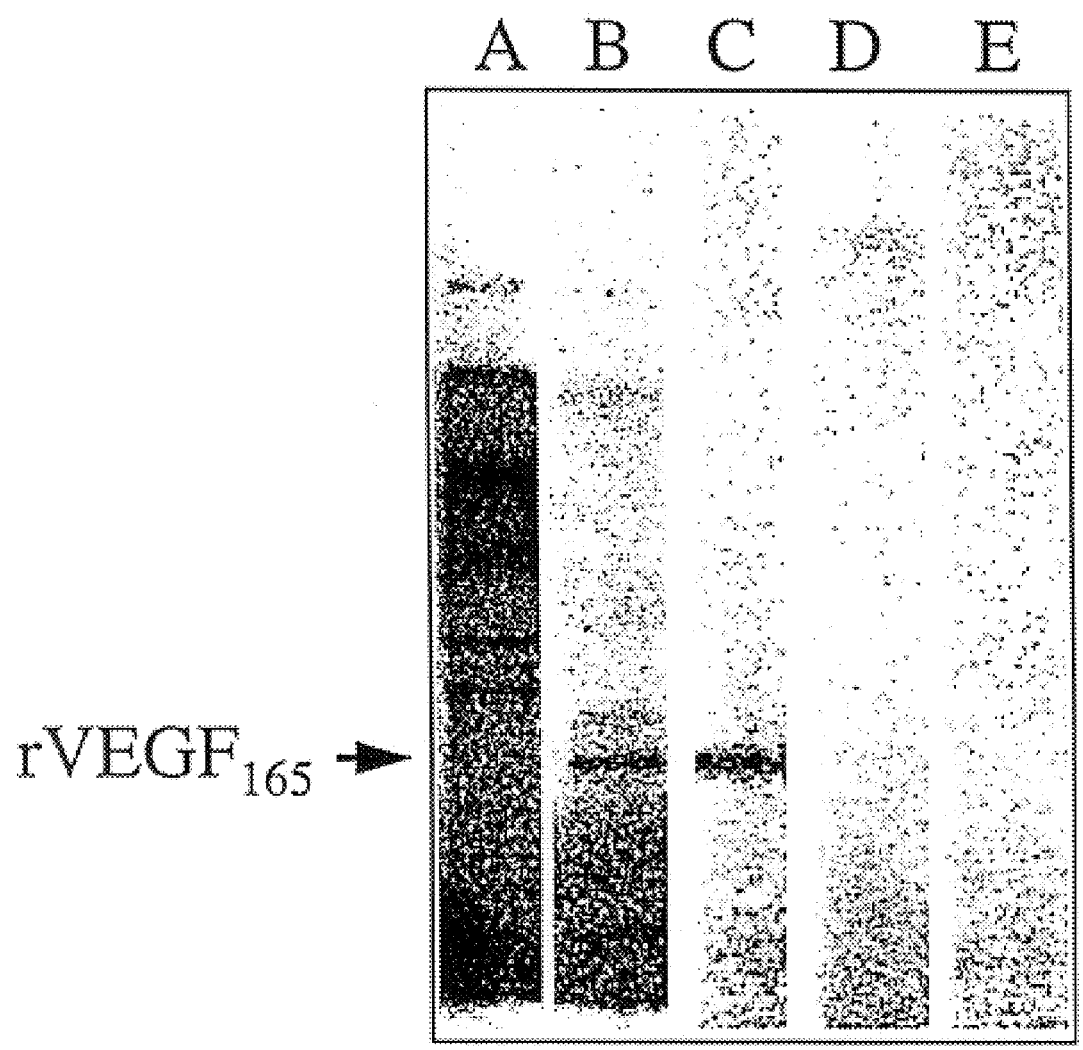
FIG. 6 illustrates ADP-Ribosylation of $rVEGF_{165}$ by bacterial toxins and by macrophage cytosolic extract.

Labeling of rVEGF with $^{32}$P-NAD was observed using cholera toxin and macrophage cytosolic extracts (FIG. 6). Labeling with cholera toxin resulted in a single $^{32}$P-labeled band corresponding to the size of rVEGF$_{165}$ standard (FIG. 6C). Labeling with macrophage cytosolic extracts resulted in the $^{32}$P-labeling of a large number of bands, due to the endogenous labeling of macrophage cytosolic proteins (FIG. 6A). To clearly demonstrate labeling of rVEGF$_{165}$ in this mixture, immunoprecipitation of the macrophage cytosolic labeling mixture with anti-VEGF antibody was necessary. Following immunoprecipitation, a prominent labeled band corresponding to rVEGF$_{165}$ was clearly visible (FIG. 6B). This band was not present in control reactions carried out in the absence of rVEGF$_{165}$. Labeling of VEGF using Pertussis toxin was not observed (FIG. 6E).

Angiogenic and Anti-Angiogenic Responses in Rat Corneas

The angiogenic responses induced in rat corneas by the concentrated conditioned media from the MPMs cultured under various conditions are shown in Table 2, Medium from non-activated MPMs cultured under normoxic conditions did not induce angiogenesis. This medium did not contain anti-angiogenic activity, as the angiogenic effects of VEGF (25 ng) were unaffected by this medium. Medium from Ifnγ/LPS-activated MPMs was potently angiogenic, while medium from iNOS-inhibited Ifnγ/LPS-activated MPMs showed markedly reduced angiogenic activity. In contrast to medium from normoxic, non-activated MPM, this medium was found to contain anti-angiogenic activity, as we have reported previously (36). Medium from normoxic, lactate-treated non-activated MPMs showed significant angiogenic activity. Similarly, medium from non-activated MPMs cultured under hypoxic conditions showed significant angiogenic activity. In both these cases, a polyclonal antibody to VEGF neutralized the angiogenic activity in the conditioned media. Angiogenic responses induced by rVEGF$_{165}$ were neutralized by anti-VEGF antibody in control experiments, while those induced by bFGF (20 ng/implant) and TNFα (20 ng/implant) were unaffected.

The angiogenic responses induced by rVEGF$_{165}$ that was ADP-ribosylated using cholera toxin or MPM cytosolic extract are shown in Table 3. While control VEGF (taken through a sham labeling procedure in the absence of cholera toxin and MPM cytoplasmic extracts) strongly induced angiogenesis, both cholera toxin-mediated and MPM cytoplasmic extract-mediated ADP-ribosylated VEGF showed greatly reduced angiogenic responses, indicating that the ADP-ribosylation abrogated the angiogenic activity of the VEGF. Since the VEGF was purified from the reaction mixtures using heparin-Sepharose binding and elution, we also tested eluates from control VEGF-free reactions prepared with cholera toxin or macrophage cytosolic extract, to determine first if these extracts contained angiogenic activity in their own right, and second, if any anti-angiogenic activity might be enriched in the eluates through this procedure, and interfere with the angiogenic activity of the VEGF. The eluates were therefore tested alone, and then with the post-reaction addition of $rVEGF_{165}$. The sham eluates did not exhibit direct angiogenic activity, nor did they exhibit anti-angiogenic activity when combined with VEGF.

DISCUSSION

Figure 2:
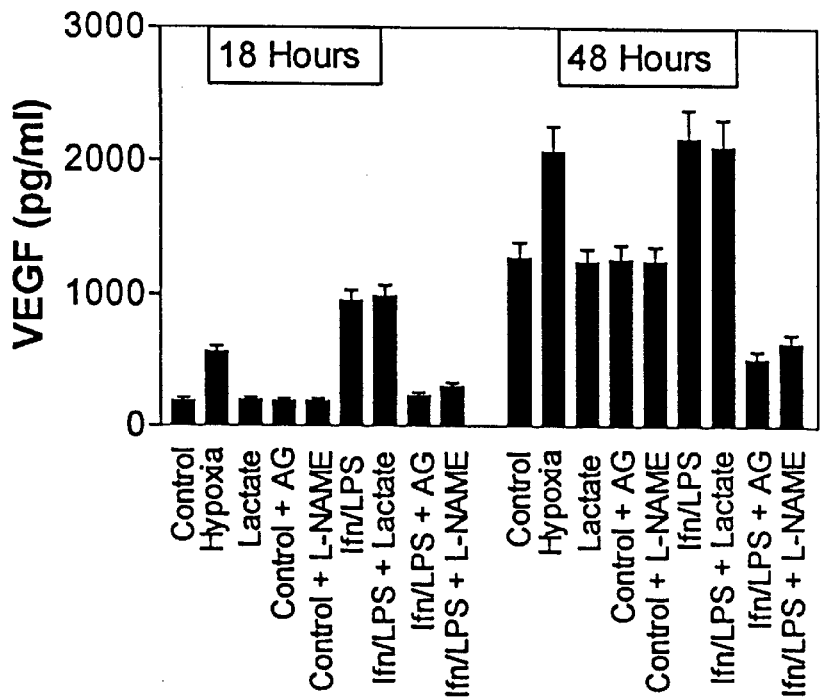
FIG. 2 illustrates VEGF production by A) RAW264.7 cells, and B) MPMs.
Figure 2:
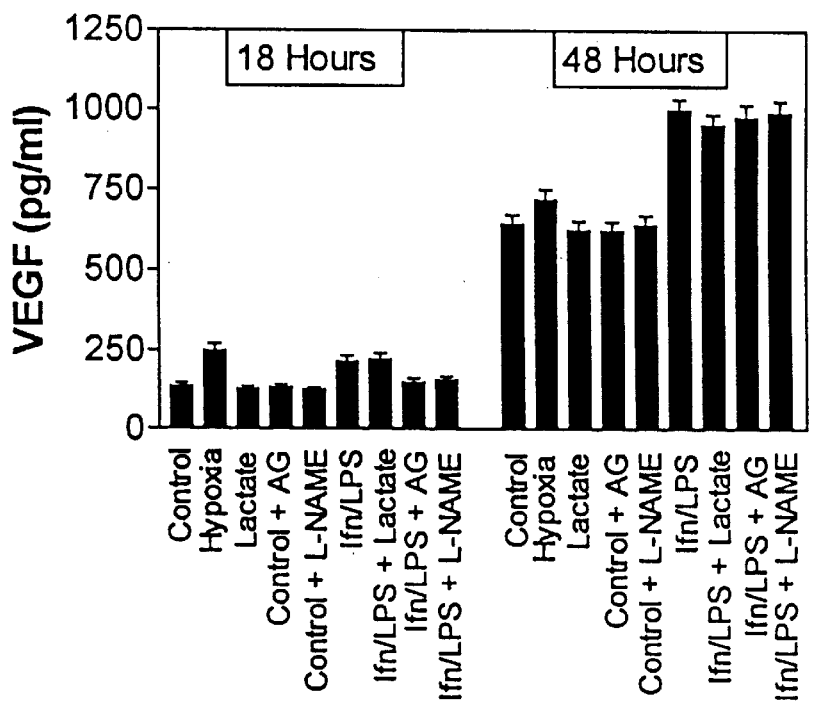

In this study, it has been shown that murine macrophages (MPMs) produce VEGF, a potent, endothelial cell specific, angiogenic growth factor (23,24). VEGF production by MPMs does not require activation, with significant VEGF levels being released into the conditioned media over 18–48 hours without the addition of external stimulants. This constitutive level of VEGF production was, however, markedly increased by stimulation of the cells with Ifnγ/LPS (FIG. 2). In contrast, the production of TNFα was strictly dependent on macrophage activation with Ifnγ and LPS, as has been shown in many previous studies (FIG. 4)(37–39).

VEGF expression has been shown to be regulated by oxygen tension both in vivo and in vitro (40–44), with low levels of oxygen (hypoxia) resulting in the upregulation of VEGF expression. This increased expression has been shown to be regulated both at the transcriptional level and at the level of mRNA stability, depending upon the cell type. In our studies, oxygen concentrations were measured in the conditioned media of macrophages cultured in both normal and Permanox culture dishes. These measurements indicated that under these conditions, the media on the MPMs and RAW cells were normoxic, suggesting that the constitutive VEGF production observed was not due to induction of VEGF gene expression by low oxygen tension. However, when cells were specifically incubated under hypoxic conditions, significant upregulation of VEGF, but not of TNFα or nitrite production, was observed in both cell types. This upregulation of VEGF expression was apparent both at the mRNA and the protein level. These observations suggest that the expression of the VEGF gene is regulated by oxygen tension in macrophages, as observed in other cell types. It is not yet clear, however, whether this regulation occurs at the level of transcription or at the level of mRNA stability.

Knighton and coworkers have shown previously that the expression of angiogenic activity by rabbit bone-marrow-derived macrophages is regulated by hypoxia, and that the high levels of lactate that accumulate in the conditioned media of hypoxic macrophages are important in regulating the expression of macrophage-derived angiogenic activity (5). In MPMs and RAW cells, culture in the presence of high lactate concentrations (25 mM), under normoxic conditions, did not modulate the level of expression of VEGF mRNA or protein. However, it is important to note that while non-stimulated MPMs express significant levels of VEGF, the conditioned media from these cells is non-angiogenic (4,8, 22). Following lactate or hypoxia treatments, the media exhibit angiogenic activity (Table 1). This raises the important question of how the angiogenic activity of VEGF is regulated. First, VEGF may operate in synergy with TNFα to stimulate the microvasculature in the conditioned media from Ifnγ/LPS-activated macrophages. However, the fact that medium from lactate-treated or hypoxia-treated non-activated macrophages, which do not contain TNFα, express potent angiogenic activity suggests that under the appropriate conditions, VEGF can be angiogenic in the absence of TNFα. This is supported by the fact that the angiogenic activity in these media is neutralized by anti-VEGF antibodies (Table 1). A second possibility tested was that medium from normoxic, non-activated MPMs might contain an anti-angiogenic factor(s) that blocks the angiogenic effects of VEGF. This hypothesis was tested using the rat corneal bio-assay, by combining concentrated conditioned medium from these cells with $rVEGF_{165}$, to determine if the angiogenic effects of the VEGF were inhibited. No inhibition of the effects of VEGF were in fact observed in this system, clearly indicating that anti-angiogenic factor(s) were not present in this conditioned medium. This is in contrast to the conditioned medium from iNOS-inhibited, Ifnγ/LPS-activated macrophage medium, as discussed further below.

It was then hypothesized that the VEGF produced by non-stimulated MPMs may differ structurally from the VEGF produced by stimulated MPMs. This structural difference could relate to alternatively spliced isoforms of VEGF with differing angiogenic activities, or to post-translational modification of VEGF by, for example, ADP ribosylation-dependent mechanisms (32,45,46). Our results using RT-PCR indicate that the isoforms of VEGF are not markedly changed during macrophage activation, by lactate, or by inhibition of iNOS. VEGF1, 2 and 3 mRNA isoforms are produced in similar proportions under all conditions tested. It thus seems that the most likely mechanism for regulation of VEGF angiogenic activity might involve post-translational mechanisms, as has been suggested recently by Hussain et al (32,47). In support of this hypothesis, rVEGF was shown to be a substrate for ADP-ribosylation, and ADP-ribosylation was shown to abrogate the angiogenic activity of rVEGF. Since macrophages are impermeable to $NAD^+$, metabolic labeling of endogenously synthesized VEGF by macrophages using $^{32}P$-labeled $NAD^+$, is not possible (32,33). However, we demonstrated labeling of $rVEGF_{165}$ in vitro, using cytosolic extracts of macrophages, as well as by the bacterial arginine-specific ADP-ribosyl transferase, cholera toxin subunit A (FIG. 6)(34,35). Pertussis toxin, on the other hand, which is a cysteine-specific ADP-ribosyl transferase, did not modify $rVEGF_{165}$ (48). In addition, we showed that ADP-ribosylation of VEGF abrogates its angiogenic activity. In contrast to unmodified $rVEGF_{165}$, $rVEGF_{165}$ derivatized using either cholera toxin or macrophage cytosolic extract was found to be non-angiogenic (Table 3).

It has been shown that the production of angiogenic activity by human monocytes and by murine macrophages is induced by activation of the cells with Ifnγ/LPS (1–3,20,21, 49). In addition, the L-arginine-dependent inducible nitric oxide synthase (iNOS)-dependent pathway plays an important role in regulating the expression of angiogenic activity by Ifnγ/LPS-activated macrophages (21). Inhibitors of iNOS, such as L-NAME, $N^g$-monomethyl-L-arginine (L-NMMA), diphenyleneiodonium (DPI) and AG block the production of angiogenic activity by activated macrophages, without inhibiting the production of the angiogenic cytokines TNFα and Il-8 (21,49,50). In this study, we show that the iNOS inhibitors L-NAME and AG markedly inhibit the production of VEGF by Ifnγ/LPS-activated RAW cells (>70% inhibition), but have little effect on the constitutive (non-stimulated) production of VEGF by these cells. Interestingly, in Ifnγ/LPS-activated RAW cells, L-NAME and AG inhibit VEGF production to a level significantly below that of non-stimulated cells. This suggests that the pathways involved in the regulation of VEGF production in non-activated and activated RAW cells are different, with only the activated pathway being sensitive to iNOS products. This might relate to the nature of the transcriptional promotors involved in the expression of the VEGF gene under constitutive and activated conditions. In MPMs, on the other hand, the iNOS inhibitors had no significant effect on the production of either the constitutive or Infγ/LPS-stimulated VEGF. However, it is again important to note that the angiogenic activity of the MPM conditioned media was markedly down-regulated by the iNOS inhibitors. Our results suggest that two mechanisms are involved in the regulation of expression of angiogenic activity by the iNOS-inhibited, Ifnγ/LPS-activated MPMs. The first is analogous to that observed in the activation of macrophages by hypoxia and lactate; namely the regulation of the ADP-ribosylation of VEGF, and hence of its angiogenic activity. Infγ/LPS activation switches the production of VEGF from the ADP-ribosylated, non-angiogenic form to the unmodified, angiogenic form. Second, the iNOS-dependent pathway regulates the expression of an inhibitor of angiogenesis. When the iNOS pathway is active and NO is produced, the inhibitor is inactive or absent; when the iNOS pathway is blocked with AG or L-NAME, the inhibitor is active. We have previously reported that this anti-angiogenic activity is present in the conditioned medium of iNOS-inhibited Ifnγ/LPS-activated MPMs (36). The nature of this inhibitor is not yet clear; however it is not neutralized by specific antibodies to thrombospondin-1 or γIP-10, both of which are potent anti-angiogenic agents that may be produced by macrophages (51,52). Specific antibodies to TNFα and TGFβ also do not neutralize the anti-angiogenic activity. The inhibitor binds weakly to heparin-Sepharose and has an apparent molecular weight >100 kDa (36).

Hussain and coworkers (32,47) have suggested that ADP-ribosylation-dependent mechanisms may be involved in the post-translational modification of angiogenic factors, resulting in non-angiogenic forms. Our results suggest that this may indeed be one of the mechanisms regulating the production of angiogenic activity by macrophages. We suggest that VEGF produced by the constitutive pathway is normally in the ADP-ribosylated, non-angiogenic form, while VEGF produced by Ifnγ/LPS-activated MPMs is in the unribosylated, angiogenic form. Activation may thus regulate the post-transcriptional modification of VEGF from the ADP-ribosylated non-angiogenic form to the unmodified angiogenic form. In addition, the iNOS pathway in activated MPMs appears to regulate the production (or bio-activity) of an anti-angiogenic factor, that is apparent only in Ifnγ/LPS-activated, iNOS-inhibited MPM medium.

These results clearly indicate that VEGF is a substrate for ADP-ribosylation, and that ADP-ribosylation of VEGF abrogates its angiogenic activity. Preliminary results (manuscript in preparation) also indicate that vitamin-K3 and novobiocin, both inhibitors of mono-ADP-ribosylation reactions (34,53), result in the production of angiogenically active VEGF by non-activated normoxic macrophages, without affecting the level of VEGF production or the production of TNFα, suggesting the involvement of mono-ADP-ribosylation in the regulation of angiogenic activity in macrophages. Ultimate proof, however, of the role of mono-ADP-ribosylation in the regulation of VEGF bio-activity by macrophages, will require the direct demonstration that VEGF is differentially ADP-ribosylated in macrophages under conditions that modify oxygen tension or Ifnγ/LPS-induced macrophage activation and the iNOS-dependent pathway.

In summary, on the basis of these observations, it appears that VEGF is an important contributor to macrophage-dependent angiogenic activity. VEGF production in macrophages is regulated at several levels. Constitutively expressed VEGF is normally angiogenically inactive. Hypoxia and Ifnγ/LPS activation increase the absolute amount of VEGF produced, but also result in the expression of angiogenic VEGF. High lactate does not increase the amount of VEGF produced, but also results in the production of angiogenic VEGF. The change in the angiogenic phenotype of VEGF may be due to post-translational modification, perhaps by the process of ADP-ribosylation, that modulates VEGF bio-activity. $rVEGF_{165}$ is a substrate for ADP-ribosylation by cholera toxin and by MPM cytoplasmic extracts, and ADP-ribosylation of $rVEGF_{165}$ was shown to abrogate its angiogenic activity. In hypoxic and Ifnγ/LPS-activated MPMs, activation upregulated VEGF mRNA expression, and also shifted the balance of post-translational modification of VEGF from the non-angiogenic to the angiogenic form. In RAW264.7 cells, the Ifnγ/LPS activation-dependent modulation of VEGF mRNA levels is regulated in part by the iNOS pathway, but the constitutive production of VEGF in non-activated cells is not. In MPMs on the other hand, the regulation of VEGF mRNA level by Ifnγ/LPS activation is not significantly dependent on the iNOS pathway. VEGF angiogenic activity in these cells appears to be regulated at the level of post-translational modification. Finally, when the iNOS pathway is inhibited in Ifnγ/LPS-activated MPMs, an anti-angiogenic factor is expressed that blocks the angiogenic activity of VEGF. Together, regulation of VEGF bio-activity by post-translational modification, and iNOS-dependent regulation of the expression an anti-angiogenic factor, provide novel mechanisms for controlling the angiogenic phenotype of macrophages, and may play a key role in the regulation of macrophage-dependent angiogenic activity in vivo, in wound repair, fibroproliferation, and possibly in solid tumor development.

The present invention is further illustrated by the following examples which are not intended to limit the effective scope of the claims. All parts and percentages in the examples and throughout the specification and claims are by weight of the final composition unless otherwise specified.

EXAMPLES

Materials & Methods

Murine Peritoneal Macrophages (MPMs) and RAW264.7 Cells

Balb-c mice (male, 6–8 weeks, Taconic, Germantown, N.Y.) were injected intraperitoneally with 2.5 ml sterile Brewer's thioglycollate broth (3% w/v) (Difco Labs., Detroit, Mich.). Five days later, the mice were sacrificed and MPMs were harvested using PBS containing 100 U/ml of heparin. Cells were centrifuged at 300 g for 5 mins. at 4° C., washed twice with serum-free DMEM, and resuspended in DMEM containing 10% FCS and 50 μg/ml gentamycin (DMEM-10% FCS). Cells were seeded into 60 mm tissue culture dishes (Costar, Cambridge, Mass.)($4\times10^6$ cells/dish)

and incubated at 37° C. in a humidified incubator in 95% air/5% $CO_2$ for 4 hrs to allow the cells to adhere. In some experiments, cells were seeded in Contur Permanox gas-permeable dishes (Miles, Naperville, Ill.) rather than regular tissue culture dishes, to increase the availability of ambient gases to the cells on the base of the dishes. Non-adherent cells were removed by washing with serum free DMEM, and the cells were refed with DMEM/1% FCS. MPMs were activated using 100 U/ml murine Ifnγ (Sigma Chemical Co., St. Louis, Mo.) and 100 ng/ml of LPS (E. coli serotype 055:B5, Sigma) either in the presence or absence of the iNOS inhibitors L-NAME (1.5 mM) or AG (1 mM). To test the effects of lactate on MPMs, sodium lactate (25 mM) was added to the cultures at the start of the incubation period. To test the effects of hypoxia, MPMs were incubated in Permanox dishes, either under normoxic conditions (95% air, 5% $CO_2$) or under hypoxic conditions (95% $N_2$, 5% $CO_2$). Media and cells were harvested at the indicated time points following addition of Ifn-γ/LPS and/or lactate. Aliquots of media were sampled immediately following incubation, and analyzed in a Blood Gas Analyzer (Instrumentation Lab., Lexington, Mass.). The remaining media were centrifuged at 4° C. for 5 mins at 15,000 g to remove cellular debris, and stored at −80° C. prior to analysis.

RAW264.7 cells were obtained from ATTC, and routinely maintained in DMEM-10% FCS. Cells were passaged by scraping, and plated in either regular or Permanox dishes, with or without Ifnγ/LPS, with or without sodium lactate, and under hypoxic conditions, as described above. The effects of L-NAME and AG on the production of VEGF and TNFα by these cells were also tested. Media and cells were harvested and treated as described above.

Isolation of Total Cellular RNA

Total cellular RNA was isolated from macrophage cell cultures using TRI REAGENT (Molecular Research Center, Inc., Cincinnati, Ohio). Medium was removed from the cells, TRI REAGENT added directly to the culture dishes, and the cell lysate passed several times through a 21 gauge syringe needle. Samples were stored at RT° for 5 mins., 0.2 ml chloroform was then added per milliliter lysis reagent, the mixture vortexed for 15 secs. and then incubated at RT° for 10 mins. The resultant mixture was centrifuged at 12,000 g for 15 mins. at 4° C. The aqueous (upper) phase was transferred to a fresh microfuge tube, and RNA precipitated by adding 0.5 ml isopropanol per 1 ml TRI REAGENT used for the original extraction. Samples were incubated at RT° for 5 mins. and then centrifuged at 12,000 g for 10 mins. at 4° C. The RNA pellets were washed with 75% ethanol, air dried for 5 mins. and dissolved in RNAase-free water.

Quantitative RT-PCR Analysis of VEGF mRNA Levels

VEGF mRNA levels were determined by RT-PCR using an internal minigene RNA standard that is present through both the RT and the PCR reaction stages. The 293 bp VEGF minigene RNA standard, containing a 69 bp gene deletion, was prepared as follows: Total RNA from MPMs was subjected to RT and PCR through 35 cycles, using the following primers:

Sense minigene primer: (18-mer) in exon 1 (positions 41–58): 5' GGACCCTGGCTTTACTGC.3'

Anti-sense minigene primer (39 mer), starting in exon 5, spanning an intron, and continuing into exon 4 to position 387, deleting 69 bp of the gene to position 318, and continuing to position 300. The primer thus spans an intron, and contains a 69 bp deletion.

5' TTGGTCTGCATTCACATCGGC-GTGATGTTGCTCTCTGAC 3'.

The PCR band was purified from primers by ethanol precipitation, and blunt end ligated into the pCR-Script AmpSK(+) vector (Stratagene, La Jolla, Calif.). The orientation of the minigene fragment in the vector was determined by dideoxy sequence analysis. A clone containing the minigene insert in an antisense orientation was used for subsequent in vitro transcription for the preparation of the RNA minigene. The vector was linearized with NotI, treated with proteinase-K (4 μg/ml) for 1 hr. at 37° C., and purified by phenol extraction and ethanol precipitation. The linearized plasmid was then transcribed in vitro using a VTRAN-7 transcription kit (Sigma), using T7 RNA polymerase, yielding sense RNA. The reaction product was treated with RNAase-free DNAase-1 (10 u/mg DNA in the transcription reaction) (Promega, Madison, Wis.) for 2 hours at 37° C. The reaction mixture was then heated to 90° C. for 5 mins., cooled, and 10× transcription stop solution (5M. ammonium acetate, 0.1M. EDTA) were added, followed by phenol extraction and isopropanol precipitation. The RNA concentration was determined spectrophotometrically. VEGF RNA minigene (2.5 pg per reaction) was then incorporated into the RT-PCR reactions. Total RNA from macrophages treated under various conditions was added to the RT-PCR reactions in amounts ranging from 1–200 ng/reaction. The oligonucleotide primers used for the competitive RT-PCR reaction were 18-mers nested into the initial primers used to prepare the minigene:

Sense primer in exon 1: 5' ACCCTGGCTTTACTGCTG 3'

Antisense primer (intron spanning): 5' GGTCTGCAT-TCACATCGG.3'

The antisense primer was used for the initial RT reaction, the reverse transcriptase was inactivated at 99° C. for 5 mins., and added to a PCR mix containing an equivalent amount of sense primer. PCR was then carried out for 25 cycles. The reactions were analyzed by electrophoresis on 1.5% agarose gels in TAE buffer, stained with ethidium bromide, and scanned using the Molecular Dynamics FluorImage Analyzer. The concentrations of input RNA that gave bands of equal intensity to that of the internal VEGF RNA minigene were then determined. Although intron-spanning primers were used throughout, controls for genomic DNA contamination of total RNA preparations were routinely carried out. These controls involved the performance of parallel reactions in the absence of reverse transcriptase.

As a control for a housekeeping gene that is not markedly modulated by the various culture conditions used, an RT-PCR procedure for the enzyme glyceraldehyde-3-phosphate dehydrogenase (G3PDH) was also developed (details not shown). Parallel reactions for G3PDH mRNA levels were performed on the various macrophage RNA samples, and the VEGF mRNA levels determined by RT-PCR were normalized to the G3PDH levels.

RT-PCR Analysis of VEGF mRNA Isoforms

For reverse transcription, 1.0 kg of total RNA was reverse transcribed using 100 ng of the reverse VEGF specific primer indicated below, using 50 U MuLv reverse transcriptase with an RNA PCR Kit (Perkin Elmer, Foster City, Calif.), following the manufacturer's protocol. Following the initial RT reaction step, the 20 μl reaction volumes were boiled for 5 mins. to inactivate the reverse transcriptase. 100 ng forward primer (see below) were added, together with 80 μl of a PCR master mix, to give a final concentration of 1 mM $MgCl_2$, 1×PCR buffer II, and 2.5 U Taq polymerase (Perkin-Elmer) per reaction. PCR primers were selected to enable the amplification of the three differentially spliced murine isoforms of VEGF mRNA formed from the VEGF gene. These VEGF mRNA isoforms are derived from a gene containing 8 exons (45). The largest, VEGF-1, is formed using all 8 exons. VEGF-2 lacks exon 7, and VEGF-3 lacks exons 6 and 7. By using PCR primers in exons 3 and 8, the three different isoforms of VEGF generate PCR amplification products of different sizes, and since they amplify from the same primers, the ratio of intensities of the three bands gives an estimate of the relative abundance of the three differentially spliced mRNA isoforms. The primers selected for the PCR amplifications were:

Forward primer, located in exon 3: 5'GATGAAGC-CCTGGAGTGC3'

Reverse Primer, located in exon 8: 5'TCCCAGAAA-CAACCCTAA3'

The following cycling program for PCR was used: Denaturation at 94° C. for 1 min., annealing at 54° C. for 1 min., and extension for 2 mins. at 72° C., for 25 cycles, with a final extension at 72° C. for 15 mins. PCR reactions were then analyzed by electrophoresis on 1.5% agarose gels using TAE buffer, and stained with ethidium bromide. Gels were scanned using a Molecular Dynamics FluorImage analyzer, and the staining intensities of the PCR-amplified VEGF isoform bands were analyzed using the ImageQuant image analysis software package (Molecular Dynamics).

Assay of VEGF Protein Levels by ELISA

VEGF in conditioned media was assayed using a sandwich ELISA kit (Quantikine M, R & D Systems, Minneapolis, Minn.), following the manufacturer's protocol. This assay detects murine VEGF with sensitivity in the range of 3–500 pg/ml. Samples with VEGF concentrations above this range were diluted with RPMI and re-assayed. All samples were assayed in triplicate. Results are presented as means+/–standard deviations of the mean (S.D.).

Assay of TNFα by ELISA

Murine TNFα was assayed using a sandwich ELISA kit (TNF-A Minikit, Endogen, Woburn, Mass.), following the procedure of the manufacturer. All samples were assayed in triplicate. Results are presented as means+/–S.D.

Assay of Nitrite

To determine the production of nitric oxide (NO) by the cells under the various conditions tested, the media were analyzed for nitrite using the Griess reaction, as described previously. Briefly, 50 µl culture medium were placed in a 96-well plate, followed by 50 µL of cold 350 mM ammonium chloride, pH 9.6. 100 µl of a mixture of 1 part 5 mM sulfanilic acid, 1 part 5 mM N-(1-Naphthyl) ethylenediamine and 3 parts glacial acetic acid was added. After 10 minutes of incubation in the dark at room temperature, absorbance at 570 nm was determined using a microplate scanner (BioTek Instruments, Burlington, Vt.). The system was calibrated using freshly-prepared standard nitrite solutions. A linear regression line was determined from the standards, and the experimental nitrite concentrations calculated. Results are means±S.D.

Assay of Angiogenic and AntiAngiogenic Activity

Conditioned media from MPM cultures were concentrated 20 fold and diafiltered using Amicon centrifugal spin filters (3 KDa cut-off)(Beverly, Mass.). Five µl concentrated media were incorporated into equal volumes of slow-release Hydron (12% w/v in 95% ethanol) (Interferon Sciences, New Brunswick, N.J.) and allowed to dry. Hydron pellets were implanted aseptically into pockets within rat corneal stromas, 2 mm from the limbal vasculature, as described previously (1,2,4,9). Corneas were examined daily for seven days using a stereomicroscope and perfused with colloidal carbon at the end of the observation period to provide a permanent record of the angiogenic responses. Corneas were examined histologically for any evidence of non-specific inflammation. Angiogenic responses were assessed on a graded scale as follows: No response, or slight budding of the limbal vasculature that regresses rapidly=0; Formation of a few capillary buds and sprouts that progress less the 0.2 mm from the limbus, and start to regress=1; Persistent growth of a network of capillary buds and sprouts that grow at least 1 mm towards the implant, but do not reach and invade the implant=2; strong growth of a dense network of capillary buds and sprouts that reaches and surrounds the implant=3. Four corneal implants were prepared per test sample, and the responses summed. A maximal response thus has a score of 12, while a minimal response has a score of 0, For the assay of anti-angiogenic activity, test conditioned media (20×concentrated) were combined with 20 ng recombinant human $VEGF_{165}$ (gift of Dr. Napoleone Ferrara, Genentech Inc., S. San Francisco, Calif.). The effects of the test media on the angiogenic activity of the rVEGF were then determined using the corneal bio-assay.

Effects of Anti-VEGF Antibodies on Macrophage Angiogenic Activity

To determine the contribution of VEGF to the angiogenic activity of the MPM conditioned media, an affinity purified neutralizing polyclonal antibody to VEGF (gift of Dr. Napoleone Ferrara) was used. Concentrated conditioned media prepared as described above were incubated with anti-VEGF antibody at a final concentration of 10 µg/ml at 37° C. for 2 hours. Controls were incubated with pre-immune IgG at the same concentration. These treated media were then assayed for angiogenic activity in the rat corneal bio-assay.

ADP-Ribosylation of rVEGF

Initial attempts to metabolically label VEGF endogenously synthesized in MPMs, using $^{32}P$-$NAD^+$ were unsuccessful, as macrophages are impermeable to $NAD^+$, which cannot enter the cells and provide a substrate for the cytoplasmic ADP-ribosyl transferases (32,33). We therefore used either permeabilized MPMs (data not shown) or macrophage cytoplasmic extracts to determine whether exogenous rVEGF is a substrate for macrophage ADP-ribosyl transferases. Similarly, rVEGF was tested as a substrate for cholera toxin (an arginine-specific ADP-ribosyl transferase) and for pertussis toxin (a cysteine-specific ADP-ribosyl transferase) (34,35).

i) Cytosolic extracts of MPMs were prepared as follows: MPMs were plated in 100 mm culture dishes ($10\times10^6$ cells per dish in 10 ml medium) in RPMI1640 medium containing 10% fetal calf serum, and incubated at 37° C. overnight. The medium was then removed, and the cells were washed (×2) with cold PBS. The cells were then harvested by scraping into cold PBS (1 ml/dish ). The cells were spun down at 300 g and resuspended on ice in 20 mM Tris-HCl pH7.5, 1 mM EDTA, 5 mM $MgCl_2$, 1 mM DTT, 2 mM mercaptoethanol, 1 mM PMSF, 1 µg/ml leupeptin, 1 µg/ml aprotinin, and 0.25M sucrose (1 ml/$50\times10^6$ cells) and sonicated briefly. The extract was centrifuged in the cold for 15 mins. at 1100 g to remove nuclei and insoluble debris. The protein content of the extracts was determined using the Bradford method (BioRad, Richmond, Calif.), and the extracts were stored at −80° C. until use. To determine whether these extracts were able to ADP-ribosylate rVEGF$_{165}$, labeling reactions were set up containing: 500 ng VEGF$_{165}$, 10 μg macrophage protein extract, 20 mM Tris-HCl pH7.8, 20 mM isoniazid, 120 mM MgCl$_2$, 10 mM NaF, 0.02% leupeptin, 0.54 mM NADP, 0.4 mM isobutyl-methylxanthine, 0.1% lubrol, 2 mM DTT, 10 mM thymidine, and 7 μCi $^{32}$P-labelled NAD$^+$ (800 Ci/mmol)(DuPont-NEN, Wilmington, Del.). After 2 hours incubation at 30° C., the reaction mixture was placed on ice, and pre-cleared for 30 mins. with 10 μl of Protein-A/G-agarose (Santa Cruz Biotech., Santa Cruz, Calif.). 10 μg of a murine anti-VEGF monoclonal antibody (gift of Texas Biotechnology, Inc., Dallas, Tex.), was added to the supernatant, and the mixture was incubated on ice for 2 hours. 10 μl Protein-A/G-agarose beads were then added, and the mixture was further incubated for 2 hours. at 4° C. with gentle rocking. The beads were harvested by centrifugation, and washed (×3) with cell lysis buffer. The beads were then incubated in an equal volume of 2× electrophoresis sample buffer (final concentration of 100 mM DTT), and heated at 95° C. for 10 mins. to elute bound VEGF from the beads. The samples were then separated using 0.1% SDS-15% PAGE, and the fractionated proteins were transferred to a nitrocellulose membrane by semi-dry electrophoretic transfer. The filters were then immunostained using anti-VEGF antibody, and the VEGF bands were detected using enhanced fluorecence detection reagents (Amersham Vistra reagents) and a Fluorimage Analyzer (Molecular Dynamics). The nitrocellulose blots were then analyzed using a PhosphorImage analyzer (Molecular Dynamics, Sunnyvale, Calif.), to determine the localization of $^{32}$P-labeled bands.

ii) rVEGF$_{165}$ was incubated for up to 2 hours at 30° C. with cholera toxin as follows: 500 ng rVEGF, 250 μg cholera toxin (A-subunit, Sigma Chemical Co., St. Louis, Mo.), in the reaction buffer described above. The reaction was terminated by the addition of an equal volume of cold 10% TCA. The precipitated protein was washed (×3) with water-saturated chloroform, and finally resuspended in an equal volume of 2× PAGE sample buffer, as above. The samples were separated by SDS-PAGE, and transferred to a nitrocellulose membrane as described above.

iii) 500 ng rVEGF$_{165}$ was incubated for up to 2 hours at 30° C. with 25 μg pertussis toxin (Sigma, cat. no. P-0317) in the reaction mixture described above. Pertussis toxin was pre-activated by incubation for 30 mins. with 10 mM ATP and 20 mM DTT prior to addition to the VEGF reaction mixture. The reaction was terminated and analyzed as described above.

Effects of ADP-Ribosylation on the Angiogenic Activity of VEGF

To determine whether ADP-ribosylation of VEGF modulates its bio-activity as an angiogenic factor, rVEGF 165 was treated as described above with either cholera toxin, or macrophage cytosolic extract, but in the presence of unlabeled NAD$^+$. To facilitate the recovery of rVEGF from the reaction mixture, rather than using immunoprecipitation for the recovery of VEGF, which requires the use of harsh, denaturing conditions for the recovery of VEGF from the Protein-A/G-agarose beads, heparin-Sepharose binding was used to recover the VEGF. Following the labeling reaction, 10 μl washed heparin-Sepharose beads were added, and the mixture was incubated at 4° C. for 4 hours with gentle agitation. The beads were then washed (×3) with 100 μl 20 mM Tris-HCl pH7.8 containing 0.4M. NaCl. VEGF was eluted from the beads by incubation with 20 μl Tris-HCl containing 1.5M. NaCl. Recovery of VEGF was determined by specific ELISA. Control reactions were carried out in the absence of bacterial toxins and macrophage extract. To ensure that anti-angiogenic activity was not present in the macrophage extracts or the cholera toxin preparations, similar labeling reactions were carried out in the absence of VEGF, and the heparin-Sepharose eluates from these reactions were tested in the anti-angiogenesis assay.

FIG. 1 illustrates the nitrite production by MPMs. Cells were incubated in DMBM/1% FCS, with or without sodium lactate (25 mM), Ifnγ (100 u/ml) and LPS (100 ng/ml), L-NAME (1.5 mM), or AG (1 mM), as indicated. Media were harvested 8, 24 and 48 hours after challenge with Ifnγ/LPS. Results are means+/−S.D. of triplicate determinations in a typical experiment. Similar results were found in at least three separate experiments.

FIG. 2 illustrates VEGF production by A) RAW264.7 cells, and B) MPMs. Cells were incubated in DMEM/1% FCS, with or without sodium lactate (25 mM), Ifnγ (100 u/ml) and LPS (100 ng/ml), L-NAME (1.5 mM), or AG (1 mM), as indicated. Media were harvested 18 and 48 hours after challenge with Ifnγ/LPS. Results are means+/−S.D. of triplicate determinations in a typical experiment. Similar results were found in at least three separate experiments.

FIG. 3 illustrates competitive RT-PCR analysis of VEGF mRNA levels in control (non-stimulated) MPMs 24 hours following plating. Varying amounts of total RNA (1–200 ng) isolated from MPMs were reverse transcribed and amplified by PCR through 25 cycles in the presence of a VEGF RNA minigene (2.5 pg) that amplifies using the same primers as the native VEGF mRNA, as described in Methods. The RNA minigene yields an amplified PCR product of 293 bp, the native VEGF mRNA yields a 362 bp fragment. The amount of total RNA that yields an amplification band of the same intensity as the minigene is determined from these analyses.

FIG. 4 illustrate RT-PCR analysis of VEGF isoforms produced by Ifnγ/LPS-activated MPMs, with or without AG treatment. Total RNA isolated from MPMs was reverse transcribed and amplified by PCR, as described in Methods. PCR primers were located in exons 3 and 8, resulting in the amplification of 3 PCR products corresponding to 652, 580 and 448 bp.

FIG. 5 illustrates TNFα production by MPMs. Cells were incubated in DMEM/1% FCS, with or without sodium lactate (25 mM), Ifnγ (100 u/ml) and LPS (100 ng/ml), L-NAME (1.5 mM), or AG (1 mM), as indicated. Media were harvested 8, 24 and 48 hours after challenge with Ifnγ/LPS. Results are means+/−S.D. of triplicate determinations in a typical experiment. Similar results were found in at least three separate experiments.

FIG. 6 illustrates ADP-Ribosylation of rVEGF$_{165}$ by bacterial toxins and by macrophage cytosolic extract. A. rVEGF (500 ng) was incubated with macrophage cytosolic extract (see Methods) in the presence of $^{32}$P-NAD$^+$. The total labeling reaction was analyzed on the 0.1% SDS-15% PAGE gel. B. The rVEGF$_{165}$-macrophage cytosolic extract labeling mixture was immuno-precipitated with anti-VEGF antibody, and the immunoprecipitated VEGF was analyzed by SDS-PAGE. A dominant $^{32}$P-labeled band migrating in the same position as rVEGF$_{165}$ (determined by Western analysis of the same blot) is indicated. C. rVEGF$_{165}$ was incubated with cholera toxin subunit A and $^{32}$P-NAD$^+$ as decribed in Methods. D. Cholera toxin was incubated with $^{32}$P-NAD$^+$ in the absence of rVEGF165, E. rVEGF$_{165}$ was incubated with pertussis toxin and $^{32}$P-NAD$^+$, as described in Methods.

TABLE 1

Relative VEGF mRNA Levels* in Macrophages Determined by Competitive RT-PCR

| | Time (hours) | | |
|---|---|---|---|
| | 4 | 10 | 24 |
| Control (unstimulated) MPMs | 1 | 1 | 1 |
| Hypoxic MPMs | 2.8 | 5 | 1.4 |
| Ifnγ/LPS-activated MPMs | 2.2 | 4.8 | 1 |
| Ifnγ/LPS-activated MPMs + AG (1 mM) | 2 | 4.7 | 1 |
| Control (unstimulated) RAW cells | 1 | 1.3 | 1.2 |
| Hypoxic RAW cells | 3 | 5.8 | 2.5 |
| Ifnγ/LPS-activated RAW cells | 2.4 | 5.4 | 2.2 |
| Ifnγ/LPS-activated RAW cells + AG (1 mM) | 0.9 | 1.4 | 1.2 |

*VEGF mRNA levels for each group are compared with the G3PDH mRNA level in the same RNA samples.

TABLE 2

Angiogenic and Anti-Angiogenic Responses Induced in Rat Corneas by Conditioned Media from Mouse Peritoneal Macrophages (MPMs) Cultured Under Various Conditions In Vitro

| Macrophage Culture Conditions[1] | Angiogenic Score[2] |
|---|---|
| 1. Normoxia | 1 |
| 2. Hypoxia | 9 |
| 3. Normoxia + Lactate (25 mM) | 8 |
| 4. Ifnγ (100 U/ml))/LPS (100 ng/ml) | 11 |
| 5. Ifnγ/LPS + Aminoguanidine (1 mM) | 2 |
| 6. Group 2 + anti-VEGF Ab (10 µg/ml) | 1 |
| 7. Group 3 + anti-VEGF Ab (10 µg/ml) | 2 |
| 8. Group 4 + anti-VEGF Ab (10 µg/ml) | 4 |
| 9. rVEGF$_{165}$ (20 ng) | 11 |
| 10. bFGF (20 ng) | 12 |
| 11. TNFα (20 ng) | 10 |
| 12. Group 9 + anti-VEGF Ab (10 µg/ml) | 2 |
| 13. Group 10 + anti-VEGF Ab (10 µg/ml) | 11 |
| 14. Group 11 + anti-VEGF Ab (10 µg/ml) | 11 |
| 15. Group 1 + rVEGF$_{165}$ (20 ng) | 11 |
| 16. Group 5 + rVEGF$_{165}$ (20 ng) | 2 |

[1]Macrophages were incubated for 48 hours under the indicated conditions, concentrated (x20) and diafiltered using Centricon 3 (3000 M.Wt. cut-off) filters (Amicon). Samples were then combined with equal volumes of Hydron (Interferon Sciences, Inc.)(12% w/v in 95% ethanol). 10 µl droplets were then allowed to dry on the cut ends of 2 mm diameter Teflon rods. These pellets were then implanted aseptically in the corneas of rats.
[2]Angiogenic responses were assessed 7 days following implantation. The angiogenic score represents the sum of the graded angiogenic responses from 4 individual corneas for each test sample. A maximal response would score 12; a minimal response 0 (see Methods).

TABLE 3

Effects of ADP-Ribosylation# on the Angiogenic Activity of rVEGF$_{165}$

| | Test Material | Angiogenic score |
|---|---|---|
| 1 | Sham-reacted rVEGF$_{165}$ (20 ng) | 11 |
| 2. | Cholera toxin-treated rVEGF$_{165}$ (20 ng) (Heparin-Sepharose eluate) | 2 |
| 3. | Cholera toxin control (Heparin-Sepharose eluate) | 1 |
| 4. | rVEGF$_{165}$ (20 ng) + Cholera toxin control | 10 |
| 5. | Macrophage cytosolic extract-treated rVEGF$_{165}$ (20 ng) (Heparin-Sepharose eluate) | 3 |
| 6. | Macrophage cytosolic extract control | 2 |
| 7. | rVEGF$_{165}$ (20 ng) + Macrophage cytosolic extract control | 11 | rVEGF$_{165}$ was treated in a reaction mixture with either cholera toxin or macrophage cytosolic extracts, as described in the Methods section. Controls of VEGF treated in the absence of cholera toxin or macrophage cytosolic extract, were performed to determine the effects of the buffers on VEGF. Controls of the cholera toxin and macrophage cytosolic.extract incubated without VEGF were also performed, to determine whether extraneous angiogenic or anti-angiogenic factors were present in these reagents. All reactions were treated with heparin-Sepharose as described in Methods, to recover the VEGF from the reaction mixtures.

Throughout this application, various publications have been referenced. The disclosures in these publications are incorporated herein by reference in order to more fully describe the state of the art.

References

1. Polverini P J, Cotran R S, Gimbrone M A Jr., Unanue, E R: Activated macrophages induce vascular proliferation. Nature 1977. 269: 804–806

2. Koch, A E; Polverini P J, Leibovich S J: Induction of neovascularization by activated human monocytes. J Leukocyte Biol 1985, 37: 279–288

3. Polverini P J: Macrophage-induced angiogenesis: A review. Cytokines. 1989, 1: 54–73

4. Polverini P J, Leibovich S J: Induction of neovascularization and nonlymphoid mesenchymal cell proliferation by macrophage cell lines. Lab Invest 1985, 51: 635–642

5. Sunderkotter C, Steinbrink K, Goebeler M, Bhardwaj R, Sorg C: Macrophages and angiogenesis. J Leukocyte Biol 1994, 55: 410–422

6. DiPietro L A, Polverini P J: Angiogenic macrophages produce the angiogenic inhibitor thrombospondin-1. Am J Pathol 1993, 143: 678–684

7. Polverini P J: The pathophysiology of angiogenesis. Crit Revs Oral Biol Med 1995, 6: 230–247

8. Folkman J: Angiogenesis in cancer, vascular, rheumatoid and other disease. Nature Med 1995, 1: 27–31

9. Leibovich S J, Polverini P J, Shepard H M, Wiseman D M, Shively V, Nuseir N: Production of angiogenic activity by human monocytes requires an L-arginine/nitric oxide synthase-dependent effector mechanism. Nature 1987, 329: 630–632

10. Koch A, Polverini P J, Kunkel S L, Harlow L A, Dipietro L A, Elner V M, Elner S G, Strieter R M: Interleukin-8 as a Macrophage-Derived Mediator of Angiogenesis. Science 1992, 258: 1798–1801

11. Frater-Schroder M, Risau W, Hallmann P, Gautschi R, Bohlen P: Tumor necrosis factor type-α, a potent inhibitor of endothelial cell growth in vitro, is angiogenic in vivo. Proc Natl. Acad Sci USA 1987, 84: 5277–5281

12. DiPietro L A, Polverini P J: Angiogenic Macrophages Produce the Angiogenic Inhibitor Thrombospondin-1, Am J Pathol 1993, 143: 678–684

13. Xiong M, Lanahan M, Elson E. Leibovich S J. P53 protein levels in murine peritoneal macrophages are modulated by the inducible-nitric oxide-synthase (iNOS) pathway. Mol Biol Cell 1996, 7(Suppl): 23a 14. Besner E B, Klagsbrun M: Macrophages Secrete a Heparin-Binding Inhibitor of Endothelial Cell Growth Microvasc Res 1991, 42:187–197

15. Polverini P J: Cytokines 1989, 1: 54–73

16. Sunderkotter C, Goebeler M Schulze-Osthoff K, Bhardwaj R, Sorg C: Macrophage-Derived Angiogenesis Factors Pharmacol Therapeut 1991, 51: 195–216

17. Nathan C F: Secretion of oxygen intermediates: Role in effector functions of activated macrophages. Fed Proc 1982, 41: 2206–2211

18. Nagashima M, Yoshiro S, Ishiwata T, Asano G: Role of vascular endothelial growth factor in angiogenesis of rheumatoid arthritis. J Rheumatol 1995, 22: 1624–1630

19. Hibbs J B Jr, Vavrin Z, Taintor R R: L-Arginine is required for the expression of the activated macrophage effector mechanism causing selective metabolic inhibition in target cells. J Immunol 1987, 138: 550–565

20. Koch A E, Cho M, Burrows J C, Polverini P J, Leibovich S J: Inhibition of production of monocyte/macrophage-derived angiogenic activity by oxygen free-radical scavengers. Cell Biol Int Reps 1992, 16: 415–411

21. Leibovich S J, Polverini P J, Fong T W, Harlow L A, Koch A E: Production of angiogenic activity by human monocytes requires an L-arginine/nitric oxide-synthase-dependent effector mechanism. Proc Natl Acad Sci USA 1994, 91: 4190–4194

22. Knighton D R, Hunt T K, Scheuenstahl H, Halliday B J, Werb Z, Banda M J: Oxygen tension regulates the expression of angiogenesis factor by macrophages. Science 1984, 221: 1283–1285

23. Leung D W, Cachianes G, Kuang W J, Goeddel D V, Ferrara N: Vascular endothelial growth factor is a secreted angiogenic mitogen. Science 1989, 244: 1306–1309

24. Connolly D T, Olander J V, Heuvelman D, Nelson R, Monsell R, Siegel N, Haymore B L, Leimgruber R, Feder J: Human vascular permeability factor. J Biol Chem 1989, 264: 20017–20024

25. Gospodarowicz D, Abraham J A, Schilling J: Isolation and characterization of a vascular endothelial cell mitogen produced by pituitary-derived folliculostellate cells. Proc Natl Acad Sci. USA 1989, 86: 7311–7315

26. Berse B, Brown L F, Van de Water L, Dvorak H F, Senger D R: Vascular Permeability Factor (Vascular Endothelial Growth Factor) Gene Is Expressed Differentially in Normal Tissues, Macrophages, and Tumors. Mol Biol Cell 1992, 3: 211–220

27. Sharkey A M, Charnock-Jones D S, Boocock C A, Brown, K D, Smith S K: Expression of mrna for vascular endothelial growth factor in human placenta. J Reprod Fertil 1993, 99: 609–615

28. Fava R A, Olsen N J, Spencer-Green G, Yeo T K, Berse B, Jackman R W, Senger D R, Dvorak H F, Brown L F: Vascular permeability factor/endothelial growth factor (VPF/VEGF): accumulation and expression in human synovial fluids and rheumatoid synovial tissue. J Exp Med. 1994, 180: 341–346

29. Torry R J, Labarrere C A, Torry D S, Holt V J, Faulk W P: Vascular endothelial growth factor expression in transplanted human hearts. Transplantation 1995, 60: 1451–1457

30. McLaren J, Prentice A, Charnock-Jones D S, Millican S A, Muller K H, Sharkey A M, Smith S K: Vascular endothelial growth factor is produced by peritoneal fluid macrophages in endometriosis and is regulated by ovarian steroids. J Clin Invest 1996, 98: 482–489

31. Shima D T, Kuroki M, Deutsch U, Ng Y S, Adamis A P, D'Amore P A: The mouse gene for vascular endothelial growth factor. J Biol Chem 1996, 271: 3877–3887

32. Zabel, D D, Feng J J, Scheuenstahl H, Hunt T K, Hussain M Z. Lactate stimulation of macrophage-derived angiogenic activity is associated with inhibition of poly (ADP-ribose) synthesis. Lab Invest 1996, 74: 644–649.

33. Aktories K, Just I: In vitro ADP-ribosylation of Rho by bacterial ADP-ribosyl transferases. Methods in Enzymol. 1995, 256: 184–195

34. Okazaki I J, Moss J: Mono-ADP-ribosylation: A reversible post-translational modification of proteins. Adv Pharmacol 1996, 35: 247–280

35. Moss J, Vaughan M: Mechanism of action of cholaregen. Evidence for ADP-ribosyl transferase activity with arginine as an acceptor. J Biol Chem 1997, 252: 2455–2457

36. Leibovich S J, Xiong M, Elson E, Sharma S, Seo C, Lanahan M: The role of macrophages in the control of angiogenesis in wound repair: Nitric oxide (NO), angiogenesisinhibitors and tumor suppresser genes. In: Bone Formation and Repair. eds. Rabie A M, Urist M R. 1997, 101–111

37. Beutler B, Cerami A: Cachectin and tumor necrosis factor as two sides of the same biological coin. Nature 1986, 320: 584–588

38. Burchett S K, Weaver W M, Westall J A, Larsen A, Kronheim S, Wilson C B: Regulation of tumor necrosis factor/cachectin and Il-1 secretion in human mononuclear phagocytes. J Immunol 1988, 140: 3473–3481

39. Mukaida N, Harada A, Yasumoto K, Matsushima K: Properties of pro-inflammatory cell type-specific leukocyte chemotactic cytokines, interleukin-8 (IL-8) and monocyte chemotactic and activating factor (MCAF). Microbiol Immunol 1992, 36: 773–789

40. Shweiki D, Itin A, Soffer D, Keshet E: Patterns of expression of vascular endothelial growth factor (VEGF) and VEGF receptors in mice suggest a role in hormonally regulated angiogenesis. Nature 1992, 359: 843–845

41. Ladoux A, Frelin C: Hypoxia is a strong inducer of vascular endothelial growth factor messenger RNA expression in the heart. Biochem Biophys Res Comms 1993, 195: 1005–1010

42. Goldberg M A, Schneider T J: Similarities between the oxygen-activated sensing mechanisms regulating the expression of vascular endothelial growth factor and erythropoietin. J Biol Chem 1994, 269: 4355–4359

43. Shima D T, Adamis A P, Ferrara N, Yeo K T, Allende R, Folkman, J, D'Amore P: Hypoxic induction of endothelial cell growth factors in retinal cells: identification and characterisation of vascular endothelial growth factor (VEGF) as the mitogen. Mol Med 1995, 1: 182–193

44. Levy A P, Levy N S, Wegner S, Goldberg M A: Transcriptional regulation of the rat vascular endothelial growth factor gene by hypoxia. J Biol Chem 1995, 270: 13333–13340

45. Brune B, Lapetina E G: Activation of a cytosolic ADP-ribosyl transferase by nitric oxide-generating agents. J Biol Chem 1989, 264: 8455–8458

46. Molina-Vedia L, McDonald B, Reep B, Brune B, DiSilvio M, Billiar T R, Lapetina E G Nitric oxide induced S-nitrosylation of glyceraldehyde-3-phosphate dehydrogenase inhibits enzymatic activity and increases endogenous ADP-ribosylation. J Biol Chem 1992, 267: 24929–24932

47. Feng J J, Hunt T K, Ghani P, Hussain M Z: Macrophage-derived angiogenic activity potential can be reversibly inhibited by ADP-ribosylation. Wound Repair Regeneration 1997, 5: A111

48. West R E, Moss J, Vaughan M, Liu T-Y: Pertussis toxin-catalyzed ADP-ribosylation of transducin. Cysteine 347 is the ADP-ribose acceptor site. J Biol Chem 1985, 260: 14428–14430

49. Leibovich S J, Golczewski J: Expression of inducible nitric oxide synthase (iNOS) is required for production of angiogenic activity by murine macrophages and IC-21 cells. Mol Biol Cell (Suppl): 373a 50. Upperman J S, Leibovich S J, Xiong M, Golczewski, J, Deitch E A Diphenyleneiodonium (DPI), an inhibitor of nucleotide-requiring flavoproteins, inhibits the production of macrophage-derived angiogenic activity. Surg Forum 1996, 47: 708–710.

51. Good D J, Polverini P J, Rastinejad F, LeBeau M M, Lemons R S, Frazier W A, Bouck N P: A tumor suppresser-dependent inhibitor of angiogenesis is immunologically indistinguishable from a fragment of thrombospondin. Proc. Natl. Acad Sci. USA 1990, 87: 6624–6628.

52. Angiolillo A L, Sgadari C, Taub D D, Liao F, Farber J M, Maheshawari S, Kleinman H K, reaman G H, Tosato G: Human interferon-inducible protein 10 is a potent inhibitor of angiogenesis in vivo. J Exp Med 1995, 182: 155–159

53. Banasik M, Ueda K: Inhibitors and activators of ADP-ribosylation reactions. Mol. Cell Biochem 1994, 138: 185–197.

Throughout this disclosure, applicant will suggest various theories or mechanisms by which applicant believes the components in the therapeutic wound healing compositions function to inhibit adenosine diphosphate-ribosylation of vascular endothelial growth factor. While applicant may offer various mechanisms to explain the present invention, applicant does not wish to be bound by theory. These theories are suggested to better understand the present invention but are not intended to limit the effective scope of the claims.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for healing a wound in a mammal which comprises the steps of:
   (A) providing a therapeutic wound healing composition consisting essentially of a therapeutically effective amount of an inhibitor of mono-adenosine diphosphate-ribosyl transferase to inhibit adenosine diphosphate-ribosylation of vascular endothelial growth factor, wherein the inhibitor of mono-adenosine diphosphate-ribosyl transferase is selected from the group consisting of Vitamin K1, Vitamin K3, Novobiocin, and silybin; and
   (B) contacting the therapeutic wound healing composition with a wound in a mammal to thereby heal the wound.

2. The method according to claim 1, wherein the mammal is man.

3. The method according to claim 1, wherein the inhibitor of mono-adenosine diphosphate-ribosyl transferase is present in the therapeutic wound healing composition in an amount from about 0.1% to about 10%, by weight of the therapeutic wound healing composition.

4. The method according to claim 1, wherein the wound is selected from the group consisting of pressure ulcers, decubitus ulcers, diabetic ulcers, and burn injuries.

5. The method according to claim 1, wherein the therapeutic wound healing composition further comprises a pharmaceutically acceptable carrier.

6. A method for treating diaper dermatitis in a human which comprises the steps of:
   (A) providing a therapeutic diaper dermatitis wound healing composition consisting essentially of:
      (a) a therapeutically effective amount of an inhibitor of mono-adenosine diphosphate-ribosyl transferase to inhibit adenosine diphosphate-ribosylation of vascular endothelial growth factor, wherein the inhibitor of mono-adenosine diphosphate-ribosyl transferase is selected from the group consisting of Vitamin K1, Vitamin K3, Novobiocin, and silybin;
      (b) a buffering agent to maintain the pH of dermatitis in a range from about 5 to about 8; and
      (c) an anti-inflammatory agent; and
   (B) contacting the therapeutic diaper dermatitis wound healing composition with diaper dermatitis in a human to thereby heal the diaper dermatitis.

7. The method according to claim 6, wherein the inhibitor of mono-adenosine diphosphate-ribosyl transferase is present in the therapeutic wound healing composition in an amount from about 0.1% to about 10%, by weight of the therapeutic wound healing composition.

8. The method according to claim 6, wherein the buffering agent is selected from the group consisting of citric acid-sodium citrate, phosphoric acid-sodium phosphate, and acetic acid-sodium acetate.

9. The method according to claim 6, wherein the anti-inflammatory agent is selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone diproprionate, betamethasone diproprionate, hydrocortisone, cortisone, dexamethasone, predinisone, methyl prednisolone, and prednisolone.

10. The method according to claim 6, wherein the therapeutic wound healing composition further comprises a pharmaceutically acceptable carrier.

\* \* \* \* \*